(12) United States Patent
Vaya et al.

(10) Patent No.: US 7,976,871 B2
(45) Date of Patent: Jul. 12, 2011

(54) MODIFIED RELEASE COMPOSITION OF HIGHLY SOLUBLE DRUGS

(75) Inventors: Navin Vaya, Gujarat (IN); Rajesh Singh Karan, Gujarat (IN); Sunil Sadanand Nadkarni, Gujarat (IN); Vinod Kumar Gupta, Gujarat (IN)

(73) Assignee: Torrent Pharmaceuticals Limited, Ahmedabad (IN)

( * ) Notice: Subject to any disclaimer, the term of this patent is extended or adjusted under 35 U.S.C. 154(b) by 0 days.

(21) Appl. No.: 11/134,631

(22) Filed: May 19, 2005

(65) Prior Publication Data

US 2006/0018933 A1    Jan. 26, 2006

Related U.S. Application Data

(63) Continuation-in-part of application No. 10/630,348, filed on Jul. 29, 2003.

(30) Foreign Application Priority Data

Aug. 5, 2002  (IN) .............. 696/MUM/2003
Aug. 5, 2002  (IN) .............. 698/MUM/2002
Jan. 22, 2003 (IN) .............. 81/MUM/2003

(51) Int. Cl.
*A61K 9/00* (2006.01)
*A61K 9/20* (2006.01)
*A61K 9/22* (2006.01)
*A61K 9/26* (2006.01)

(52) U.S. Cl. ........ 424/469; 424/400; 424/464; 424/465; 424/468

(58) Field of Classification Search .......... None
See application file for complete search history.

(56) References Cited

U.S. PATENT DOCUMENTS

| | | | |
|---|---|---|---|
| 2,566,582 | A | 7/1951 | Rotner |
| 2,968,158 | A | 1/1961 | Ruschig et al. |
| 3,097,242 | A | 7/1963 | Hoehn et al. |
| 3,174,901 | A | 3/1965 | Sterne |
| 3,454,635 | A | 7/1969 | Weber et al. |
| 3,654,357 | A | 4/1972 | Bretschneider et al. |
| 3,668,215 | A | 6/1972 | Plumpe et al. |
| 3,669,966 | A | 6/1972 | Ambrogi |
| 3,708,486 | A | 1/1973 | Kutter et al. |
| 3,801,495 | A | 4/1974 | Gould |
| 3,957,833 | A | 5/1976 | Chodnekar et al. |
| 4,080,472 | A | 3/1978 | Bohuon |

(Continued)

FOREIGN PATENT DOCUMENTS

EP    0008203 A1    2/1980

(Continued)

OTHER PUBLICATIONS

Merck Index Online: accessed Aug. 4, 2008 for Niacin, Sodium Valproate.*

(Continued)

*Primary Examiner* — Anand U Desai
*Assistant Examiner* — Melissa S Mercier
(74) *Attorney, Agent, or Firm* — Hedman & Costigan, P.C.; James V. Costigan

(57) ABSTRACT

A novel modified release dosage form comprising of a high solubility active ingredient, which utilizes dual retard technique to effectively reduce the quantity of release controlling agents. Present invention can optionally comprise additionally another active ingredient as an immediate release form or modified release form. Present invention also relates to a process for preparing the said formulation.

4 Claims, 5 Drawing Sheets

U.S. PATENT DOCUMENTS

| | | | |
|---|---|---|---|
| 4,363,802 A | 12/1982 | Matsumura et al. | |
| 4,376,777 A | 3/1983 | Kawanatsu et al. | |
| 4,572,912 A | 2/1986 | Yoshioka et al. | |
| 4,725,610 A | 2/1988 | Meguro et al. | |
| 4,775,687 A | 10/1988 | Meguro et al. | |
| 4,791,125 A | 12/1988 | Clark | |
| 4,835,184 A | 5/1989 | Hugelin et al. | |
| 5,002,953 A | 3/1991 | Hindley | |
| 5,061,717 A | 10/1991 | Clark et al. | |
| 5,098,725 A | 3/1992 | Rotman et al. | |
| 5,104,888 A | 4/1992 | Yoshioka et al. | |
| 5,183,823 A | 2/1993 | Sohda et al. | |
| 5,225,426 A | 7/1993 | Miyaoka et al. | |
| 5,232,945 A | 8/1993 | Hulin | |
| 5,264,451 A | 11/1993 | Kees | |
| 5,306,726 A | 4/1994 | Hulin | |
| 5,334,604 A | 8/1994 | Goldstein et al. | |
| 5,399,357 A * | 3/1995 | Akiyama et al. | 424/457 |
| 5,472,704 A * | 12/1995 | Santus et al. | 424/435 |
| 5,478,852 A | 12/1995 | Olefsky et al. | |
| 5,589,492 A | 12/1996 | Haigh | |
| 5,945,125 A | 8/1999 | Kim | |
| 6,031,004 A | 2/2000 | Timmins et al. | |
| 6,048,883 A | 4/2000 | Haigh et al. | |
| 6,296,874 B1 | 10/2001 | Cutie | |
| 6,337,091 B1 | 1/2002 | Kim et al. | |
| 6,340,475 B2 | 1/2002 | Shell et al. | |
| 6,660,300 B1 * | 12/2003 | Timmins et al. | 424/469 |
| 6,790,459 B1 | 9/2004 | Cheng et al. | |
| 6,866,866 B1 | 3/2005 | Chen et al. | |
| 2004/0022849 A1 | 2/2004 | Castan et al. | |

FOREIGN PATENT DOCUMENTS

| | | |
|---|---|---|
| EP | 0155845 A1 | 9/1985 |
| EP | 0332332 A1 | 9/1989 |
| EP | 0428312 A2 | 5/1991 |
| EP | 0533933 A1 | 3/1993 |
| EP | 0842925 A1 | 5/1998 |
| WO | WO 92/18501 | 10/1992 |
| WO | WO 93/02079 | 2/1993 |
| WO | WO 93/22445 | 11/1993 |
| WO | WO 94/05659 | 3/1994 |

OTHER PUBLICATIONS

Merck Index Online, accessed Aug. 4, 2008 for Niacin and Sodium Valproate.*

* cited by examiner

MODIFIED RELEASE COMPOSITION OF HIGHLY SOLUBLE DRUGS

This application is a continuation-in-part of Ser. No. 10/630,348, filed Jul. 29, 2003.

FIELD OF INVENTION

This invention relates to a modified release dosage form comprising of a high solubility active ingredient, which utilizes dual retard technique to effectively reduce the quantity of release controlling agents. Present invention can optionally comprise additionally another active ingredient as an immediate release form or modified release form. Present invention also relates to a process for preparing the said formulation.

BACKGROUND OF THE INVENTION

It is well known to those skilled in the art that the blood levels of drugs need to be maintained above a minimum effective level and below its minimum toxic level in order to obtain the desired therapeutic effects and to minimize side effects. Unfortunately, the pharmacokinetic properties (absorption, elimination and metabolism) of most drugs are such that they need to be administered three to four times a day. This kind of a dosing regimen is very inconvenient and leads to reduction in patient compliance. Reduction of dosing regimen from three times a day (t.i.d.) to twice daily (b.i.d.) to once a day results in increased convenience and comfort and therefore increased patient compliance. Drugs that are administered in the form of conventional tablets of capsules become available to body fluids at a rate that is initially very high, followed by a rapid decline. For many drugs, this delivery pattern results in a transient overdose, followed by a long period of under dosing. This is a pattern of limited clinical usefulness. The delivery pattern was improved in the 1970's with the introduction of a variety of modified delivery systems. Modified release formulations, which are effective in maintaining the therapeutic blood levels over, extended periods of time result in optimal therapy. They not only reduce the frequency of dosing, but they also reduce the severity and frequency of side effects, as they maintain substantially constant blood levels and avoid the fluctuations associated with the conventional immediate release formulations administered three to four times a day.

There are a number of different modified release dosage forms available commercially. However, some of these are expensive to manufacture and can be difficult to swallow, particularly in elderly patients. Many of these modified delivery systems utilize hydrophilic, polymeric matrices that provide useful levels of control to the delivery of sparingly soluble drugs. For soluble drugs, however, and particularly for highly soluble drugs, such matrices do not provide adequate control over the release rate, instead resulting in a release that approximates first-order kinetics and may have a problem of dose dumping or burst release. However, since many modified release dosage forms contain comparatively large amounts of active ingredient it is often necessary to include large amounts of suitable excipients to achieve appropriate controlled release profiles. Clearly, this will tend to increase the size of the dosage form.

The various techniques to make modified release dosage form of drugs as described in prior art are as follows—

One method of prolonging the release of a highly water-soluble drug is disclosed PCT Patent application no. WO99/47128. A biphasic controlled release delivery system for metformin hydrochloride, which has prolonged gastric residence and that swells following hydration. The ratio of inner solid phase to outer continuous phase is 0.5:1 to about 4:1. The major limitation of this invention is that it provides a very bulky formulation for higher doses of the metformin hydrochloride that is very inconvenient for human consumption. For instance, example cited provides formulation of 500 mg metformin hydrochloride with tablet weight of 1.0 gm. Hence restricting to the low dose sustained release tablets of 500 mg or slightly more and making it obligatory to take two tablets of 500 mg each time to provide sustain action. The cited example teaches use of combination of atleast one hydrophilic polymer and which is a essential part for swelling. Non swellable or nonerodeble formulations are not included in the invention.

PCT application No. WO 02/28181 A1 describes a monolithic sustained release formulation of metformin hydrochloride. The method of making the formulation involves hot melt granulation followed by wet granulation with binders or extrusion. The formulation essentially requires binder and auxiliary pharmaceutically acceptable excipients. The formulation consists of metformin hydrochloride polymer and or hydrophobic material. The dosage form release more than 90% of the drug within 8 hours.

Similarly U.S. Pat. No. 6,340,475 B2 assigned to Depomed Inc. describes monolithic controlled release formulation of highly water soluble drugs including metformin hydrochloride. The formulation swells when ingested thus prolonging its residence time in the stomach. The formulations are made of hydrophilic polymers, which results in swellable and erodible matrix.

Another method of prolonging the release of a highly water-soluble drug is disclosed in International Patent application publication no. WO 96/26718, published Sep. 6, 1996. The method of this publication is the incorporation of the drug into a polymeric matrix to form a tablet that is administered orally. The polymer is water-swellable yet erodible in gastric fluids.

Similarly Chih-Ming Chen in international patent application number WO 02/36100 describes a once a formulation of metformin hydrochloride which is based on osmotically controlled technique and that is non expandable in nature and has a passage in the coating membrane for release of drug.

Kim et al. in U.S. Pat. No. 6,337,091 describes a matrix based controlled release formulation for highly soluble drugs over long periods of time. The release controlling agent is a swellable gum which encapsulates or make granules of drug, which is then disposed in more swellable erodible polymers such as HPMC or poly(ethyleneoxide).

These systems can provide for modified release for selected active ingredients like active ingredients with low dose or low water solubility. However, when a highly soluble or high dose active ingredient is used, most of these systems have the disadvantages such as comparatively low payload of active ingredient thus making dosage form bulky and expensive or lead to burst effect or prolonged release of active ingredient for a shorter duration or use of complex manufacturing procedure and/or equipment.

There exists a need for compositions and process for making orally deliverable dosage form containing highly soluble active ingredient as modified release that overcomes the problems discussed above. This invention addresses the need.

Therefore, it would be of considerable clinical benefit to design a dosage form with high pay load of highly soluble active ingredient that would be much easier for the patient to swallow. This type of technology could also be used to reduce the size of many existing drug formulations.

Therefore an object of the present invention is a modified release dosage form of high solubility active ingredient.

The second object of the present invention is a modified release dosage form with high payload of active ingredient, which is suitable for swallowing for humans.

Yet another object of the present invention is to provide a dosage form, which uses dual retard technique to control the release of the high solubility active ingredient and significantly reduce the amount of release controlling agents which are otherwise required in very high quantity and make the dosage form very bulky and therefore pose difficulty in swallowing.

A further object of the present invention is to provide a dosage form, which gives accurate dosing and is simple to prepare.

A further object of the present invention is to provide a dosage form, which can be given twice a day or more preferably can be given once a day.

A further object of the present invention is to provide a dosage form, which can optionally comprise additionally another active ingredient as an immediate release form or modified release form.

SUMMARY OF THE INVENTION

The above objects are realized by a dosage form, which comprises of a) Micro matrix particles containing high solubility active ingredient and one or more hydrophobic release controlling agent, b) Coating of Micro matrix particles with one or more hydrophobic release controlling agents. It may optionally also include one or more commonly used excipients in oral pharmaceutical formulations. The present invention also provides solid oral dosage form comprising a composition according to the invention. Optionally, it may also comprise additionally another active ingredient as an immediate release form or modified release form.

The present invention also teaches the use of dual retard technique to effectively control the release rate of modified release active ingredient by using small quantity of release controlling agents. This dual retard technique thus sufficiently reduces the size of the dosage form, which is convenient for swallowing.

The present invention further teaches the use of hydrophobic release controlling agents.

The present invention also provides a novel process for preparing the novel formulations of the invention.

The present invention further provides a method of treating an animal, particularly a human in need of treatment utilizing the active agents, comprising administering a therapeutically effective amount of composition or solid oral dosage form according to the invention to provide administration of active ingredients.

DETAILED DESCRIPTION OF THE INVENTION

This invention relates to a modified release dosage form comprising of a high solubility active ingredient prepared by using dual retard technique to control the release of the high solubility active ingredient and to increase the payload of high solubility active ingredient The term "modified release" as used herein in relation to the composition according to the invention or a rate controlling polymer or used in any other context means release, which is not immediate release and is taken to encompass controlled release, sustained release, prolonged release, timed release, retarded release, extended release and delayed release. The term "modified release dosage form" as used herein can be described as dosage forms whose drug-release characteristics of time course and/or location are chosen to accomplish therapeutic or convenience objectives not offered by conventional dosage forms such as a solution or an immediate release dosage form. Modified release solid oral dosage forms include both delayed and extended release drug products (as per US FDA guideline for 'SUPAC-MR: Modified Release Solid Oral Dosage Forms').

The term "dosage form" denotes any form of the formulation that contains an amount sufficient to achieve a therapeutic effect with a single administration.

The term "active ingredient" refers to an agent, active ingredient compound or other substance, or compositions and mixture thereof that provide some pharmacological, often beneficial, effect. Reference to a specific active ingredient shall include where appropriate the active ingredient and it's pharmaceutically acceptable salts.

The term "high solubility" as used herein in relation to active agent means that from less than 1 part to 300 parts of water or less than 1 part to 30 parts of water will be required to dissolve 1 part of active ingredient.

The invention provides a novel modified release dosage form of high solubility active ingredient, which utilizes dual retard technique to effectively reduce the quantity of release controlling agents and a process for preparing the dosage form.

The dosage form comprises of a) Micro matrix particles containing, high solubility active ingredient and one or more hydrophobic release controlling agent, b) Coating of Micro matrix particles with one or more hydrophobic release controlling agents. It may optionally also include one or more commonly used excipients in oral pharmaceutical formulations. The release of high solubility active ingredient is controlled through dual retard technique. The dual retard technique is a combination of matrix formulations and reservoir formulations. First the micromatrix particles of high solubility dose active ingredient and one or more hydrophobic release controlling agents are formed and then these are further coated with one or more release controlling agents. Thus the dual retard release technique presents the double barriers and effectively controls the diffusion of the high solubility active ingredients from the present invention in predictable manner and also significantly reduces the amount of release controlling agents which are otherwise required in very high quantity and make the dosage form very bulky and therefore pose difficulty in swallowing. The other advantages of the present invention are such as it reduces the chances of dose dumping, unnecessary burst effects and failure of the system, which are otherwise usually associated with simple matrix or reservoir systems.

Optionally, it may also contain another active ingredient as an immediate release form or modified release form.

The high solubility active ingredient can be present in the form of a free base or in the form of pharmaceutically acceptable salts. Pharmaceutically acceptable salts forming part of this invention are intended to define but not limited to salts of the carboxylic acid moiety such as alkali metal salts like Li, Na and K salts; alkaline earth metal salts like Ca and Mg salts; salts of organic bases such as lysine, arginine, guanidine, diethanolamine, choline, and the like; ammonium or substituted ammonium salts and aluminium salts. Salts may be acid addition salts which defines but not limited to sulfates, nitrates, phosphates, perchlorates, borates, hydrohalides, acetates, tartrates, maleates, citrates, succinates, palmoates, methanesulfonates, benzoates, salicylates, hydroxynaphthoates, benzensulfonates, ascorbates, glycerophosphates, ketoglutarates and the like.

Further, high solubility active ingredient, where applicable, may be present either in the form of one substantially optically pure enantiomer or as a mixture of enantiomers or polymorphs thereof.

The high solubility active ingredients comprises of the following therapeutic classes but not limited to adrenergic agent; adrenocortical steroid; adrenocortical suppressant; aldosterone antagonist; amino acid; anabolic; analeptic; analgesic; anesthetic; anorectic; anti-acne agent; anti-adrenergic; anti-allergic; anti-amebic; anti-anemic; anti-anginal; anti-arthritic; anti-asthmatic; anti-atherosclerotic; antibacterial; anticholinergic; anticoagulant; anticonvulsant; antidepressant; antidiabetic; antidiarrheal; antidiuretic; anti-emetic; anti-epileptic; antifibrinolytic; antifungal; antihemorrhagic; antihistamine; antihyperlipidemia; antihypertensive; antihypotensive; anti-infective; anti-inflammatory; antimicrobial; antimigraine; antimitotic; antimycotic, antinauseant, antineoplastic, antineutropenic, antiparasitic; antiproliferative; antipsychotic; antirheumatic; antiseborrheic; antisecretory; antispasmodic; antithrombotic; anti-ulcerative; antiviral; appetite suppressant; blood glucose regulator; bone resorption inhibitor; bronchodilator; cardiovascular agent; cholinergic; depressant; diagnostic aid; diuretic; dopaminergic agent; estrogen receptor agonist; fibrinolytic; fluorescent agent; free oxygen radical scavenger; gastric acid supressant; gastrointestinal motility effector; glucocorticoid; hair growth stimulant; hemostatic; histamine H2 receptor antagonists; hormone; hypocholesterolemic; hypoglycemic; hypolipidemic; hypotensive; imaging agent; immunizing agent; immunomodulator; immunoregulator; immunostimulant; immunosuppressant; keratolytic; LHRH agonist; mood regulator; mucolytic; mydriatic; nasal decongestant; neuromuscular blocking agent; neuroprotective; NMDA antagonist; non-hormonal sterol derivative; plasminogen activator; platelet activating factor antagonist; platelet aggregation inhibitor; psychotropic; radioactive agent; scabicide; sclerosing agent; sedative; sedative-hypnotic; selective adenosine A1 antagonist; serotonin antagonist; serotonin inhibitor; serotonin receptor antagonist; steroid; thyroid hormone; thyroid inhibitor; thyromimetic; tranquilizer; amyotrophic lateral sclerosis agent; cerebral ischemia agent; Paget's disease agent; unstable angina agent; vasoconstrictor; vasodilator; wound healing agent; xanthine oxidase inhibitor.

Examples of high solubility active ingredients comprises of but not limited to Abacavir sulfate; Aminocaproic acid; Alendronate sodium; Amitriptyline hydrochloride; Amphetamine; Acetaminophen; Atropine sulfate; Balsalazide; Benzepril hydrochloride; Bisoprolol fumarate; Bupropion hydrochloride; Buformin; Captopril; Cetrizine hydrochloride; Ciprofloxacin; Clindamycin; Chlorpheniramine maleate; Chlorpromazine hydrochloride; Clomipramine hydrochloride; Clonidine hydrochloride; Clopidogrel bisulfate; Cloxacillin Sodium; Codeine phosphate; Colchicines; Cyclophosphamide; Diethylcarbamazine citrate; DL-methionine; Eprosartan; Ethembutol hydrochloride; Ethosuximide; Erythromycin; Ferrous sulfate; Fluoxetine hydrochloride; Fosinopril sodium; Gabapentin; Hydralazine hydrochloride; Hydrocodone bitartrate; Hydroxyzine hydrochloride; Hydroxyurea; Indinavir sulfate; Isoniazid; Isosorbide moninitrate; Lactobionate; Lamivudine; Levamisole hydrochloride; Levofloxacin; Lisinopril; Losartan potassium; Metformin hydrochloride; Methylphenidate hydrochloride; Metoprolol tartrate; Minocycline hydrochloride; Montelukast sodium; Naproxen sodium; Neostigmine bromide; Nicotinamide; Niacin; Nifurtimox; Nortriptyline hydrochloride; Olanzepine; Oxybytynin chloride; Penicillamine; Penicillin V potassium; Phenytoin sodium; Phenformin; Pravastatin sodium; Potassium chloride; Primaquine phosphate; Promethazine; Promethazine hydrochloride; Proponolol hydrochloride; Propoxyphene hydrochloride; Pseudophedrine hydrochloride; Pyridostigmine bromide; Pyridoxine hydrochloride; Quinapril hydrochloride; Quetiapine; Ramipril; Ranitidine hydrochloride; Risedronate sodium; Rosiglitazone maleate; Sodium valproate; Salbutamol sulfate; Stavudine; Sumatriptan succinate; Terazosin hydrochloride; Tetracycline hydrochloride; Timolol meleate; Tramodol hydrochloride; Valacyclovir hydrochloride; Vancomycin; Venlafaxine hydrochloride; acetylsalicylic acid; acyclovir; allopurinol; amlodipine besylate; amoxicillin; atenolol; atorvastatin calcium; azithromycin; carbidopa; carisoprodol; cefprozil; celecoxib; cephalaxin; cimetidine; citalopram hydrobromide; clindamycin hydrochloride; cyclobenzaprine hydrochloride; desloratidine; doxazosin mesylate; doxycycline; enalapril maleate; famotidine; fexofenadine hydrochloride; fluconazole; folic acid; irbesartan; levodopa; levonorgestrel; levothyroxine sodium; lorazepam; meclizine hydrochloride; metaxalone; metronidazole; mirtazepine; nitrofurantoin; nystatin; oxycodone hydrochloride; paracetamol; paroxetine hydrochloride; prednisolone quetiapine fumerate; raloxifene; hydrochloride; risperidone; sertraline hydrochloride; sildenafil citrate; simvastatin; tamoxifen citrate; tamsulosin hydrochloride; temazepam; tolterodine tartrate; topiramate; trazodone hydrochloride; trimethoprim; valsartan; zolpidem tartrate; Verapamil hydrochloride; Wafarin sodium and the active ingredients described in U.S. Pat. Nos. 2,968,158, 3,097,242, 3,454,635, 3,654,357, 3,668,215, 3,669,966, 3,708,486, 3,801,495, 5,104,888, 5,232,945, 5,264,451, 5,478,852, 6,296,874, 3,957,853, 4,080,472, 3,174,901, 4,835,184, 6,031,004 and European patent publication numbers EP0008203, EP0032128, EP0139421, EP0155845, EP0177353, EP0208420, EP0257881, EP0306228, EP0319189, EP0332331, EP0332332, EP0428312, EP0489663, EP0508740, EP0528734, EP0533933, EP0833933, EP87112480.6 and Japanese patent number 05271204 and United Kingdom patent numbers 5504078, GB2088365A and PCT patent application numbers WO91/19702, WO92/03425, WO92/18501, WO93/02079, WO93/21166, WO93/22445, WO94/01420, WO94/05659.

The quantity of the high solubility active ingredient for e.g. as mentioned above can be less than or equal to 1500 mg.

A dosage form of the present invention may optionally contain more than one high solubility active ingredient.

A dosage form of the present invention may optionally contain more than one antidiabetic active ingredient.

As indicated above the outer portion of the present invention may comprise auxiliary excipients such as for example lubricants, plasticisers, anti-tack agents, opacifying agents, pigments, and such like. As will be appreciated by those skilled in the art, the exact choice of excipient and their relative amounts will depend to some extent on the final oral dosage form.

Suitable lubricants, including agents that act on the flowability of the powder to be compressed are, for example, colloidal slilcon dioxide such as Aerosil 200 (Aerosil is a Trade Mark); talc; stearic acid, magnesium stearate, calcium stearate and sodium stearyl fumarate.

In micro matrix particles, the active ingredient and one or more hydrophobic release controlling agents are preferably present in a ratio of from 100:1 to 100:75, more particularly from 100:2.5 to 100:50, still more preferably from 100:2.5 to 100:30 and most preferably from 100:2.5 to 100:20.

Micro matrix particles and coating of one or more hydrophobic release controlling agents are preferably present in a ratio of from 100:0.5 to 100:75, more particularly from 100:2.5 to 100:50, still more preferably from 100:2.5 to 100:30 and most preferably from 100:2.5 to 100:20.

According to one embodiment the release controlling agents are pharmaceutically excipients, which are hydrophobic in nature.

The polymers that can be used to form the rate-controlling membrane or micromatrix are described in greater detail herein below.

The hydrophobic release controlling agents are selected from but are not limited to Ammonio methacrylate copolymers type A and B as described in USP, methacrylic acid copolymer type A, B and C as described in USP, Polyacrylate dispersion 30% as described in Ph. Eur., Polyvinyl acetate dispersion, ethylcellulose, cellulose acetate, cellulose propionate (lower, medium or higher molecular weight), cellulose acetate propionate, cellulose acetate butyrate, cellulose acetate phthalate, cellulose triacetate, poly(methyl methacrylate), poly(ethyl methacrylate), poly(butyl methacrylate), poly(isobutyl methacrylate), and poly(hexyl methacrylate). Poly(isodecyl methacrylate), poly(lauryl methacrylate), poly(phenyl methacrylate), poly(methyl acrylate), poly(isopropyl acrylate), poly(isobutyl actylate), poly(octadecyl acrylate), waxes such as beeswax, carnauba wax, microcrystalline wax, and ozokerite; fatty alcohols such as cetostearyl alcohol, stearyl alcohol; cetyl alcohol and myristyl alcohol; and fatty acid esters such as glyceryl monostearate, glyceryl distearate, glycerol monooleate, acetylated monoglycerides, tristearin, tripalmitin, cetyl esters wax, glyceryl palmitostearate, glyceryl behenate, and hydrogenated castor oil.

According to an especially preferred embodiment the release controlling agent contains ammonio methacrylate copolymers and fatty acid esters as hereinafter described.

The suitable hydrophobic agents are polymers sold under the Trade Mark Eudragit RS (Ammonio Methacrylate Copolymer type B USP), Eudragit NE 30D (Polyacrylate dispersion 30% Ph., Eur.), Eudragit RL (Ammonio Methacrylate Copolymer type A USP) and Kollicoat SR 30 D and fatty acid esters such as glyceryl behenate, and hydrogenated castor oil. Eudragit polymers are polymeric lacquer substances based on acrylate and/or methacrylates.

The dosage form can also include one or more commonly used excipients in oral pharmaceutical formulations.

Representative commonly used excipients in oral pharmaceutical formulations include talc, fumed silica, glyceryl monostearate, magnesium stearate, calcium stearate, kaolin, colloidal silica, gypsum, Tween 80, Geleol pastiles (trade mark), micronised silica and magnesium trisilicate.

The quantity of commonly used excipients in oral pharmaceutical formulations used is from about 2% to about 500% by weight, preferably from 2 to 100% more particularly 10 to 60% based on the total dry weight of the polymer.

The dosage form can also include a material that improves the processing of the release controlling agents. Such materials are generally referred to as "plasticisers" and include, for example, adipates, azelates, benzoates, citrates, isoebucaes, phthalates, sebacates, stearates, tartrates, polyhydric alcohols and glycols.

Representative plasticisers include acetylated monoglycerides; butyl phthalyl butyl gylcolate; dibutyl tartrate; diethyl phthalate; dimethyl phthalate; ethyl phthalyl ethyl glycolate; glycerin; ethylene glycol, propylene glycol; Triethyl citrate; triacetin; tripropinoin; diacetin; dibutyl phthalate; acetyl monoglyceride; polyethylene glycols; castor oil; triethyl citrate; polyhydric alcohols, acetate esters, glycerol triacetate, acetyl triethyl citrate, dibenzyl phthalate, dihexyl phthalate, butyl octyl phthalate, diisononyl phthalate, butyl octyl phthalate, dioctyl azelate, epoxidised tallate, triisoctyl trimellitate, diethylexyl phthalate, di-n-octyl phthalate, di-I-octyl phthalate, di-I-decyl phthalate, di-n-undecyl phthalate, di-n-tridecyl phthalate, tri-2-ethylexyl trimellitate, di-2-ethylexyl adipate, di-2-ethylhexyl sebacate, di-2-ethylhexyl azelate, dibutyl sebacate, glyceryl monocaprylate, glycerol distearate, glyceryl monocaprate, nicotine, oxybutamine chloride, perinodopril erbumine, pilocorpine, poldine methyl sulfate and zalcitane.

The amount of plasticiser to be used is from about 1% to 50% based on the weight of the dry release controlling agent(s).

The amount of release controlling agent(s) to be used in forming the outer portion will be determined based on various parameters such as the desired delivery properties, including the amount of active ingredient to be delivered, the active ingredient release rate desired, and the size of the micro matrix particles.

Part comprising another active ingredient—It comprises of active ingredient(s) and includes one or more commonly used excipients in oral immediate release or modified release pharmaceutical formulations.

The active ingredient(s) can be present in the form of a free base or in the form of pharmaceutically acceptable salts. Pharmaceutically acceptable salts forming part of this invention are intended to define but not limited to salts of the carboxylic acid moiety such as alkali metal salts like Li, Na and K salts; alkaline earth metal salts like Ca and Mg salts; salts of organic bases such as lysine, arginine, guanidine, diethanolamine, choline, and the like; ammonium or substituted ammonium salts and aluminium salts. Salts may be acid addition salts which defines but not limited to sulfates, nitrates, phosphates, perchlorates, borates, hydrohalides, acetates, tartrates, maleates, citrates, succinates, palmoates, methanesulfonates, benzoates, salicylates, hydroxynaphthoates, benzensulfonates, ascorbates, glycerophosphates, ketoglutarates and the like.

Further, active ingredient(s), where applicable, may be present either in the form of one substantially optically pure enantiomer or as a mixture of enantiomers or polymorphs thereof.

The active ingredient(s) comprises of the following therapeutic classes but not limited to adrenergic agent; adrenocortical steroid; adrenocortical suppressant; aldosterone antagonist; amino acid; anabolic; analeptic; analgesic; anesthetic; anorectic; anti-acne agent; anti-adrenergic; anti-allergic; anti-amebic; anti-anemic; anti-anginal; anti-arthritic; anti-asthmatic; anti-atherosclerotic; antibacterial; anticholinergic; anticoagulant; anticonvulsant; antidepressant; antidiabetic; antidiarrheal; antidiuretic; anti-emetic; anti-epileptic; antifibrinolytic; antifungal; antihemorrhagic; antihistamine; antihyperlipidemia; antihypertensive; antihypotensive; anti-infective; anti-inflammatory; antimicrobial; antimigraine; antimitotic; antimycotic, antinauseant, antineoplastic, antineutropenic, antiparasitic; antiproliferative; antipsychotic; antirheumatic; antiseborrheic; antisecretory; antispasmodic; antithrombotic; anti-ulcerative; antiviral; appetite suppressant; blood glucose regulator; bone resorption inhibitor; bronchodilator; cardiovascular agent; cholinergic; depressant; diagnostic aid; diuretic; dopaminergic agent; estrogen receptor agonist; fibrinolytic; fluorescent agent; free oxygen radical scavenger; gastric acid supressant; gastrointestinal motility effector; glucocorticoid; hair growth stimulant; hemostatic; histamine H2 receptor antagonists; hormone; hypocholesterolemic; hypoglycemic; hypolipidemic; hypotensive; imaging agent; immunizing agent; immunomodulator; immunoregulator; immunostimulant; immunosuppressant; keratolytic; LHRH agonist; mood regulator; mucolytic; mydriatic; nasal decongestant; neuromuscular blocking agent; neuroprotective; NMDA antagonist; non-hormonal sterol derivative; plasminogen activator; platelet activating factor antagonist; platelet aggregation inhibitor; psychotropic; radioactive agent; scabicide; sclerosing agent; sedative; sedative-hypnotic; selective adenosine A1 antagonist; serotonin antagonist; serotonin inhibitor; serotonin receptor antagonist; steroid; thyroid hormone; thyroid inhibitor; thyromimetic; tranquilizer; amyotrophic lateral sclerosis agent; cerebral ischemia agent; Paget's disease agent; unstable angina agent; vasoconstrictor; vasodilator; wound healing agent; xanthine oxidase inhibitor.

Examples of active ingredient comprises of but not limited to—16-alpha fluorocstradiol, 16alpha-gitoxin, 16-epiestriol, 17 alpha dihydroequilenin, 17 alpha estradiol, 17 beta estradiol, 17 hydroxy progesterone, 1alpha-hydroxyvitamin D2, 1-dodecpyrrolidinone, 20-epi-1,25dihydroxyvitamin D3, 22-oxacalcitriol, 2CVV, 2'-nor-cGMP, 3-isobutyl GABA, 5-ethynyluracil, 6-FUDCA, 7-methoxytacrine, Abamectin, abanoquil, abecarnil, abiraterone, Ablukast, Ablukast Sodium, Acadesine, acamprosate, Acarbose, Acebutolol, Acecainide Hydrochloride, Aceclidine, aceclofenae, Acedapsone, Aceglutamide Aluminum, Acemannan, Acetaminophen, Acetazolamide, Acetohexamide, Acetohydroxamic Acid, acetomepregenol, Acetophenazine Maleate, Acetosulfone Sodium, Acetylcholine Chloride, Acetylcysteine, acetyl-L-carnitine, acetylmethadol, Acifran, acipimox, acitemate, Acitretin, Acivicin, Aclarubicin, aclatonium, Acodazole Hydrochloride, aconiazide, Acrisorcin, Acrivastine, Acronine, Actisomide, Actodigin, Acyclovir, acylfulvene, adafenoxate, adapalene, Adapalene, adatanserin, Adatanserin Hydrochloride, adecypenol, adecypenol, Adefovir, adelmidrol, ademetionine, Adenosine, Adinazolam, Adipheinine Hydrochloride, adiposin, Adozelesin, adrafinil, Adrenalone, airbutamine, alacepril, Alamecin, Alanine, Alaproclate, alaptide, Albendazole, albolabrin, Albuterol, Albutoin, Alclofenae, Alclometasone Dipropionate, Alcloxa, aldecalmycin, Aldesleukin, Aldioxa, Alendronate Sodium, alendronic acid, alentemol, Alentemol Hydrobromide, Aletamine Hydrochloride, Aleuronium Chloride, Alexidine, alfacalcidol, Alfentanil Hydrochloride, alfuzosin, Algestone Acetonide, alglucerase, Aliflurane, alinastine, Alipamide, Allantoin, Allobarbital, Allopurinol, ALL-TK antagonists, Alonimid, alosetron, Alosetron Hydrochloride, Alovudine, Alpertine, Alpha Amylase, alpha idosone, Alpidem, Alprazolam, Alprenolol Hydrochloride, Alprenoxime Hydrochloride, Alprostadil, Alrestatin Sodium, Altanserin Tartrate, Alteplase, Althiazide, Altretamine, altromycin B, Alverinc Citrate, Alvircept Sudotox, Amadinone Acetate, Amantadine Hydrochloride, ambamustine, Ambomycin, Ambruticin, Ambuphylline, Ambuside, Amcinafal, Amcinonide, Amdinocillin, Amdinocillin Pivoxil, Amedalin Hydrochloride, amelometasone, Ameltolide, Amesergide, Ametantrone Acetate, amezinium metilsulfate, amfebutamone, Amfenac Sodium, Amflutizole, Amicycline, Amidephrine Mesylate, amidox, Amifloxacin, amifostine, Amikacin, Amiloride Hydrochloride, Aminacrine Hydrochloride, Aminobenzoate Potassium, Aminobenzoate Sodium, Aminocaproic Acid, Aminoglutethimide, Aminohippurate Sodium, aminolevulinic acid, Aminophylline, Aminorex, Aminosalicylate sodium, Aminosalicylic acid, Amiodarone, Amiprilose Hydrochloride, Amiquinsin Hydrochloride, amisulpride, Amitraz, Amitriptyline Hydrochloride, Amlexanox, amlodipine, Amobarbital Sodium, Amodiaquine, Amodiaquine Hydrochloride, Amorolfine, Amoxapine, Amoxicillin, Amphecloral, Amphetamine Sulfate, Amphomycin, Amphotericin B, Ampicillin, ampiroxicam, Ampyzine Sulfate, Amquinate, Amrinone, amrinone, amrubicin, Amsacrine, amylin, amythiamicin, Anagestone Acetate, anagrelide, Anakinra, ananain, anaritide, Anaritide Acetate, Anastrozole, Anazolene Sodium, Ancrod, andrographolide, Androstenedione, angiogenesis inhibitors, Angiotensin Amide, Anidoxime, Anileridine, Anilopam Hydrochloride, Aniracetam, Anirolac, Anisotropine Methylbromide, Anistreplase, Anitrazafen, anordrin, antagonist D, antagonist G, antarelix, Antazoline Phosphate, Anthelmycin, Anthralin, Anthramycin, antiandrogen, Acedapsone, Felbamate, antiestrogen, antineoplaston, Antipyrine, antisense oligonucleotides, apadoline, apafant, Apalcillin Sodium, apaxifylline, Apazone, aphidicolin glycinate, Apixifylline, Apomorphine Hydrochloride, apraclonidine, Apraclonidine Hydrochloride, Apramycin, Aprindine, Aprindine Hydrochloride, aprosulate sodium, Aprotinin, Aptazapine Maleate, aptiganel, apurinic acid, apurinic acid, aranidipine, Aranotin, Arbaprostil, arbekicin, arbidol, Arbutamine Hydrochloride, Arclofenin, Ardeparin Sodium, argatroban, Arginine, Argipressin Tannate, Arildone, aripiprazol, arotinolol, Arpinocid, Arteflene, Artilide Fumarate, asimadoline, aspalatone, Asparaginase, Aspartic Acid, Aspartocin, asperfuran, Aspirin, aspoxicillin, Asprelin, Astemizole, Astromicin Sulfate, asulacrine, atamestane, Atenolol, atevirdine, Atipamezole, Atiprosin Maleate, Atolide, Atorvastatin Calcium, Atosiban, Atovaquone, atpenin B, Atracurium Besylate, atrimustine, atrinositol, Atropine, Auranofin, aureobasidin A, Aurothioglucose, Avilamycin, Avoparcin, Avridine, Axid, axinastatin 1, axinastatin 2, axinastatin 3, Azabon, Azacitidinie, Azaclorzine Hydrochloride, Azaconazole, azadirachtine, Azalanstat Dihydrochloride, Azaloxan Fumarate, Azanator Maleate, Azanidazole, Azaperone, Azaribine, Azaserine, azasetron, Azatadine Maleate, Azathioprine, Azathioprine Sodium, azatoxin, azatyrosine, azelaic acid, azelastine, azelnidipine, Azepindole, Azetepa, azimilide, Azithromycin, Azlocillin, Azolimine, Azosemide, Azotomycin, Aztreonam, Azumolene Sodium, Bacampicillin Hydrochloride, baccatin III, Bacitracin, Baclofen, bacoside A, bacoside B, bactobolamine, balanol, balazipone, balhimycin, balofloxacin, balsalazide, Bambermycins, bambuterol, Bamethan Sulfate, Bamifylline Hydrochloride, Bamnidazole, baohuoside 1, Barmastine, barnidipine, Basifungin, Batanopride Hydrochloride, batebulast, Batelapine Maleate, Batimastat, beauvericin, Becanthone Hydrochloride, becaplermin, becliconazole, Beclomethasone Dipropionate, befloxatone, Beinserazide, Belfosdil, Belladonna, Beloxamide, Bemesetron, Bemitradine, Bemoradan, Benapryzine Hydrochloride, Benazepril Hydrochloride, Benazeprilat, Bendacalol Mesylate, Bendazac, Bendroflumethiazide, benflumetol, benidipine, Benorterone, Benoxaprofen, Benoxaprofen, Benoxinate Hydrochloride, Benperidol, Bentazepam, Bentiromide, Benurestat, Benzbromarone, Benzethonium Chloride, Benzetimide Hydrochloride, Benzilonium Bromide, Benzindopyrine Hydrochloride, benzisoxazole, Benzocaine, benzochlorins, Benzoctamine Hydrochloride, Benzodepa, benzoidazoxan, Benzonatate, Benzoyl Peroxide, Benzoylpas Calcium, benzoylstaurosporine, Benzquinamide, Benzthiazide, benztropine, Benztropine Mesylate, Benzydamine Hydrochloride, Benzylpenicilloyl Polylysine, bepridil, Bepridil Hydrochloride, Beractant, Beraprost, Berefrine, berlafenone, bertosamil, Berythromycin, besipirdine, betaalethine, betaclamycin B, Betamethasone, betamipron, betaxolol, Betaxolol Hydrochloride, Bethanechol Chloride, Bethanidine Sulfate, betulinic acid, bevantolol, Bevantolol Hydrochloride, Bezafibrate, bFGF inhibitor, Bialamicol Hydrochloride, Biapenem, Bicalutamide, Bicifadine Hydrochloride, Biclodil Hydrochloride, Bidisomide, bifemelane, Bifonazole, bimakalim, bimithil, Bindarit, Biniramycin, binospirone, bioxalomycin alpha2, Bipenamol Hydrochloride, Biperiden, Biphenamine Hydrochloride, biriperone, bisantrene, bisaramil, bisaziridinylspermine, bis-benzimidazole A, bis-benzimidazole B, bisnafide, Bisobrin Lactate, Bisoprolol, Bispyrithione Magsulfex, bistramide D, bistramide K, bistratene A, Bithionolate Sodium, Bitolterol Mesylate, Bivalirudin, Bizelesin, Bleomycin Sulfate, Bolandiol Dipropionate, Bolasterone, Boldenone Undecylenate, boldine, Bolenol, Bolmantalate, bopindolol, Bosentan, Boxidine, brefeldin, breflate, Brequinar Sodium, Bretazenil, Bretylium Tosylate, Brifentanil Hydrochloride, brimonidine, Brinolase, Brocresine, Brocrinat, Brofoxine, Bromadoline Maleate, Bromazepam, Bromchlorenone, Bromelains, bromfenac, Brominidione, Bromocriptine, Bromodiphenhydramine Hydrochloride, Bromoxanide, Bromperidol, Bromperidol Decanoate, Brompheniramine Maleate, Broperamole, Bropirimine, Brotizolam, Bucainide Maleate, bucindolol, Buclizine Hydrochloride, Bucromarone, Budesonide, budipine, budotitane, Buformin, Bumetanide, Bunaprolast, bunazosin, Bunolol Hydrochloride, Bupicomide, Bupivacaine Hydrochloride, Buprenorphine Hydrochloride, Bupropion Hydrochloride, Buramate, Buserelin Acetate, Buspirone Hydrochloride, Busulfan, Butabarbital, Butacetin, Butaclamol Hydrochloride, Butalbital, Butamben, Butamirate Citrate, Butaperazine, Butaprost, Butedronate Tetrasodium, butenafine, Buterizine, buthionine sulfoximine, Butikacin, Butilfenin, Butirosin Sulfate, Butixirate, butixocort propionate, Butoconazole Nitrate, Butonate, Butopamine, Butoprozine Hydrochloride, Butorphanol, Butoxamine Hydrochloride, Butriptyline Hydrochloride, Cactinomycin, Cadexomer Iodine, Caffeine, calanolide A, Calcifediol, Calcipotriene, calcipotriol, Calcitonin, Calcitriol, Calcium Undecylenate, calphostin C, Calusterone, Cambendazole, camonagrel, camptothecin derivatives, canarypox IL-2, candesartan, Candicidin, candoxatril, candoxatrilat, Caniglibose, Canrenoate Potassium, Canrenone, capecitabine, Capobenate Sodium, Capobenic Acid, Capreomycin Sulfate, capromab, capsaicin, Captopril, Capuride, Caracemide, Carbachol, Carbadox, Carbamazepine, Carbamide Peroxide, Carbantel Lauryl Sulfate, Carbaspirin Calcium, Carbazeran, carbazomycin C, Carbenicillin Potassium, Carbenoxolone Sodium, Carbetimer, carbetocin, Carbidopa, Carbidopa-Levodopa, Carbinoxamine Maleate, Carbiphene Hydrochloride, Carbocloral, Carbocysteine, Carbol-Fuchsin, Carboplatin, Carboprost, carbovir, carboxamide-amino-triazo-le, carboxyamidotriazole, carboxymethylated beta-1,3-glucan, Carbuterol Hydrochloride, CaRest M3, Carfentanil Citrate, Carisoprodol, Carmantadine, Carmustine, CARN 700, Carnidazole, Caroxazone, carperitide, Carphenazine Maleate, Carprofen, Carsatrin Succinate, Cartazolate, carteolol, Carteolol Hydrochloride, cartilage derived inhibitor, Carubicin Hydrochloride, Carumonam Sodium, carvedilol, carvotroline, Carvotroline Hydrochloride, carzelesin, casein kinase inhibitors (ICOS), castanospermine, caurumonam, cebaracetam, cecropin B, Cedefingol, Cefaclor, Cefadroxil, Cefamandole, Cefaparole, Cefatrizine, Cefazaflur Sodium, Cefazolin, Cefbuperazone, cefcapene pivoxil, cefdaloxime pentexil tosilate, Cefdinir, cefditoren pivoxil, Cefepime, cefetamet, Cefetecol, cefixime, cefluprenam, Cefmenoxime Hydrochloride, Cefmetazole, cefminlox, cefodizime, Cefonicid Sodium, Cefoperazone Sodium, Ceforanide, cefoselis, Cefotaxime Sodium, Cefotetan, cefotiam, Cefoxitin, cefozopran, cefpimizole, Cefpiramide, cefpirome, cefpodoxime proxetil, cefprozil, Cefroxadine, cefsulodin, Ceftazidime, cefteram, ceftibuten, Ceftizoxime Sodium, ceftriaxone, Cefuroxime, celastrol, celikalim, celiprolol, cepacidiine A, Cephacetrile Sodium, Cephalexin, Cephaloglycin, Cephaloridine, Cephalothin Sodium, Cephapirin Sodium, Cephradine, cericlamine, cerivastatin, Ceronapril, certoparin sodium, Ceruletide, Cetaben Sodium, Cetalkonium Chloride, Cetamolol Hydrochloride, cetiedil, cetirizine, Cetophenicol, Cetraxate Hydrochloride, cetrorelix, Cetylpyridinium Chloride, Chenodiol, Chlophedianol Hydrochloride, Chloral Betaine, Chlorambucil, Chloramphenicol, Chlordantoin, Chlordiazepoxide, Chlorhexidine Gluconate, chlorins, Chlormadinone Acetate, chloroorienticin A, Chloroprocaine Hydrochloride, Chloropropamide, Chloroquine, chloroquinoxaline sulfonamide, Chlorothiazide, Chlorotrianisene, Chloroxine, Chloroxylenol, Chlorphenesin Carbamate, Chlorpheniramine Maleate, Chlorpromazine, Chlorpropamide, Chlorprothixene, Chlortetracycline Bisulfate, Chlorthalidone, Chlorzoxazone, Cholestyramine Resin, Chromonar Hydrochloride, cibenzoline, cicaprost, Ciclafrine Hydrochloride, Ciclazindol, ciclesonide, cicletanine, Ciclopirox, Cicloprofen, cicloprolol, Cidofovir, Cidoxepin Hydrochloride, Cifenline, Ciglitazone, Ciladopa Hydrochloride, cilansetron, Cilastatin Sodium, Cilazapril, cilnidipine, Cilobamine Mesylate, cilobradine, Cilofungin, cilostazol, Cimaterol, Cimetidine, cimetropium bromide, Cinalukast, Cinanserin Hydrochloride, Cinepazet Maleate, Cinflumide, Cingestol, cinitapride, Cinnamedrine, Cinnarizine, cinolazepam, Cinoxacin, Cinperene, Cinromide, Cintazone, Cintriamide, Cioteronel, Cipamfylline, Ciprefadol Succinate, Ciprocinonide, Ciprofibrate, Ciprofloxacin, ciprostene, Ciramadol, Cirolemycin, cisapride, cisatracurium besilate, Cisconazole, Cisplatin, cis-porphyrin, cistinexine, citalopram, Citenamide, citicoline, citreamicin alpha, cladribine, Clamoxyquin Hydrochloride, Clarithromycin, clausenamide, Clavulanate Potassium, Clazolam, Clazolimine, clebopride, Clemastine, Clentiazem Maleate, Clidinium Bromide, clinafloxacin, Clindamycin, Clioquinol, Clioxanide, Cliprofen, clobazam, Clobetasol Propionate, Clobetasone Butyrate, Clocortolone Acetate, Clodanolene, Clodazon Hydrochloride, clodronic acid, Clofazimine, Clofibrate, Clofilium Phosphate, Clogestone Acetate, Clomacran Phosphate, Clomegestone Acetate, Clometherone, clomethiazole, clomifene analogues, Clominorex, Clomiphene, Clomipramine Hydrochloride, Clonazepam, Clonidine, Clonitrate, Clonixeril, Clonixin, Clopamide, Clopenthixol, Cloperidone Hydrochloride, clopidogrel, Clopimozide, Clopipazan Mesylate, Clopirac, Cloprednol, Cloprostenol Sodium, Clorazepate Dipotassium, Clorethate, Clorexolone, Cloroperone Hydrochloride, Clorprenaline Hydrochloride, Clorsulon, Clortermine Hydrochloride, Closantel, Closiramine Aceturate, Clothiapine, Clothixamide Maleate Cloticasone Propionate, Clotrimazole, Cloxacillin Benzathine, Cloxyquin, Clozapine, Cocaine, Coccidioidin, Codeine, Codoxime, Colchicine, colestimide, Colestipol Hydrochloride, Colestolone, Colforsin, Colfosceril Palmitate, Colistimethate Sodium, Colistin Sulfate, collismycin A, collismycin B, Colterol Mesylate, combretastatin A4, combretastatin analogue, complestatin, conagenin, Conorphone Hydrochloride, contignasterol, contortrostatin, Cormethasone Acetate, Corticorelin Ovine Triflutate, Corticotropin, Cortisone Acetate, Cortivazol, Cortodoxone, cosalane, costatolide, Cosyntropin, cotinine, Coumadin, Coumermycin, crambescidin 816, Crilvastatin, crisnatol, Cromitrile Sodium, Cromolyn Sodium, Crotamiton, cryptophycin 8, cucumariosid, Cuprimyxin, curacin A, curdlan sulfate, curiosin, Cyclacillin, Cyclazocine, cyclazosin, cyclic HPMPC, Cyclindole, Cycliramine Maleate, Cyclizine, Cyclobendazole, cyclobenzaprine, cyclobut A, cyclobut G, cyclocapron, Cycloquanil Pamoate, Cycloheximide, cyclopentanthraquinones, Cyclopenthiazide, Cyclopentolate Hydrochloride, Cyclophenazine Hydrochloride, Cyclophosphamide, cycloplatam, Cyclopropane, Cycloserine, cyclosin, Cyclosporine, cyclothialidine, Cyclothiazide, cyclothiazomycin, Cyheptamide, cypemycin, Cypenamine Hydrochloride, Cyprazepam, Cyproheptadine Hydrochloride, Cyprolidol Hydrochloride, cyproterone, Cyproximide, Cysteamine, Cysteine Hydrochloride, Cystine, Cytarabine, Cytarabine Hydrochloride, cytarabine ocfosfate, cytochalasin B, cytolytic factor, cytostatin, Dacarbazine, dacliximab, dactimicin, Dactinomycin, daidzein, Daledalin Tosylate, dalfopristin, Dalteparin Sodium, Daltroban, Dalvastatin, danaparoid, Danazol, Dantrolene, daphlnodorin A, dapiprazole, dapitant, Dapoxetine Hydrochloride, Dapsone, Daptomycin, Darglitazone Sodium, darifenacin, darlucin A, Darodipine, darsidomine, Daunorubicin Hydrochloride, Dazadrol Maleate, Dazepinil Hydrochloride, Dazmegrel, Dazopride Fumarate, Dazoxiben Hydrochloride, Debrisoquin Sulfate, Decitabine, deferiprone, deflazacort, Dehydrocholic Acid, dehydrodidemnin B, Dehydroepiandrosterone, delapril, Delapril Hydrochloride, Delavirdine Mesylate, delequamine, delfaprazine, Delmadinone Acetate, delmopinol, delphinidin, Demecarium Bromide, Demeclocycline, Demecycline, Demoxepam, Denofungin, deoxypyridinoline, Depakote, deprodone, Deprostil, depsidomycin, deramciclane, dermatan sulfate, Desciclovir, Descinolone Acetonide, Desflurane, Desipramine Hydrochloride, desirudin, Deslanoside, deslorelin, desmopressin, desogestrel, Desonide, Desoximetasone, desoxoamiodarone, Desoxycorticosterone Acetate, detajmium bitartrate, Deterenol Hydrochloride, Detirelix Acetate, Devazepide, Dexamethasone, Dexamisole, Dexbrompheniramine Maleate, Dexchlorpheniramine Maleate, Dexclamol Hydrochloride, Dexetimide, Dexfenfluramine Hydrochloride, dexifosfamide, Deximafen, Dexivacaine, dexketoprofen, dexloxiglumide, Dexmedetomidine, Dexormaplatin, Dexoxadrol Hydrochloride, Dexpanthenol, Dexpemedolac, Dexpropranolol Hydrochloride, Dexrazoxane, dexsotalol, dextrin 2-sulphate, Dextroamphetamine, Dextromethorphan, Dextrorphan Hydrochloride, Dextrothyroxine Sodium, dexverapamil, Dezaguanine, dezinamide, dezocine, Diacetolol Hydrochloride, Diamocaine Cyclamate, Diapamide, Diatrizoate Meglumine, Diatrizoic Acid, Diaveridine, Diazepam, Diaziquone, Diazoxide, Dibenzepin Hydrochloride, Dibenzothiophene, Dibucaine, Dichlorvos, Dichloralphenazone, Dichlorphenamide, Dicirenone, Diclofenac Sodium, Dicloxacillin, dicranin, Dicumarol, Dicyclomine Hydrochloride, Didanosine, didemnin B, didox, Dienestrol, dienogest, Diethylcarbamazine Citrate, diethylhomospermine, diethylnorspermine, Diethylpropion Hydrochloride, Diethylstilbestrol, Difenoximide Hydrochloride, Difenoxin, Diflorasone Diacetate, Difloxacin Hydrochloride, Difluanine Hydrochloride, Diflucortolone, Diflumidone Sodium, Diflunisal, Difluprednate, Diftalone, Digitalis, Digitoxin, Digoxin, Dihexyverine Hydrochloride, dihydrexidine, dihydro-5-azacytidine, Dihydrocodeine Bitartrate, Dihydroergotamine Mesylate, Dihydroestosterone, Dihydrostreptomycin Sulfate, Dihydrotachysterol, dihydrotaxol, 9-, Dilantin, Dilevalol Hydrochloride, Diltiazem Hydrochloride, Dimefadane, Dimefline Hydrochloride, Dimenhydrinate, Dimercaprol, Dimethadione, Dimethindene Maleate, Dimethisterone, dimethyl prostaglandin Al, Dimethyl Sulfoxide, dimethylhomospermine, dimiracetam, Dimoxamine Hydrochloride, Dinoprost, Dinoprostone, Dioxadrol Hydrochloride, dioxamycin, Diphenhydramine Citrate, Diphenidol, Diphenoxylate Hydrochloride, diphenyl spiromustine, Dipivefin Hydrochloride, Dipivefrin, dipliencyprone, diprafenone, dipropylnorspermine, Dipyridamole, Dipyrithione, Dipyrone, dirithromycin, discodermolide, Disobutamide, Disofenin, Disopyramide, Disoxaril, disulfiram, Ditekiren, Divalproex Sodium, Dizocilpine Maleate, Dobutamine, docarpamine, Docebenone, Docetaxel, Doconazole, docosanol, dofetilide, dolasetron, Ebastine, ebiratide, ebrotidine, ebselen, ecabapide, ecabet, ecadotril, ecdisteron, echicetin, echistatin, Echothiophate Iodide, Eclanamine Maleate, Eclazolast, ecomustine, Econazole, ecteinascidin 722, edaravone, Edatrexate, edelfosine, Edifolone Acetate, edobacomab, Edoxudine, edrecolomab, Edrophonium Chloride, edroxyprogesteone Acetate, efegatran, eflornithine, efonidipine, egualcen, Elantrine, eleatonin, elemene, eletriptan, elgodipine, eliprodil, Elsamitrucin, eltenae, Elucaine, emalkalim, emedastine, Emetine Hydrochloride, emiglitate, Emilium Tosylate, emitefur, emoctakin, Enadoline Hydrochloride, enalapril, Enalaprilat, Enalkiren, enazadrem, Encyprate, Endralazine Mesylate, Endrysone, Enflurane, englitazone, Enilconazole, Enisoprost, Enlimomab, Enloplatin, Enofelast, Enolicam Sodium, Enoxacin, enoxacin, enoxaparin sodium, Enoxaparin Sodium, Enoximone, Enpiroline Phosphate, Enprofylline, Enpromate, entacapone, enterostatin, Enviradene, Enviroxime, Ephedrine, Epicillin, Epimestrol, Epinephrine, Epinephryl Borate, Epipropidine, Epirizole, epirubicin, Epitetracycline Hydrochloride, Epithiazide, Epoetin Alfa, Epoetin Beta, Epoprostenol, Epoprostenol Sodium, epoxymexrenone, epristeride, Eprosartan, eptastigmine, equilenin, Equilin, Erbulozole, erdosteine, Ergoloid Mesylates, Ergonovine Maleate, Ergotamine Tartrate, ersentilide, Ersofermin, erythritol, Erythrityl Tetranitrate, Erythromycin, Esmolol Hydrochloride, Esorubicin Hydrochloride, Esproquin Hydrochloride, Estazolam, Estradiol, Estramustine, estramustine analogue, Estrazinol Hydrobromide, Estriol, Estrofurate, estrogen agonists, estrogen antagonists, Estrogens, Conjugated, Estrogens, Esterified, Estrone, Estropipate, esuprone, Etafedrine Hydrochloride, Etanidazole, etanterol, Etarotene, Etazolate Hydrochloride, Eterobarb, ethacizin, Ethacrynate Sodium, Ethacrynic Acid, Ethambutol Hydrochloride, Ethamivan, Ethanolamine Oleate, Ethehlorvynol, Ether, Ethinyl estradiol, Ethiodized Oil, Ethionamide, Ethonam Nitrate, Ethopropazine Hydrochloride, Ethosuximide, Ethotoin, Ethoxazene Hydrochloride, Ethybenztropine, Ethyl Chloride, Ethyl Dibunate, Ethylestrenol, Ethyndiol, Ethynerone, Ethynodiol Diacetate, Etibendazole, Etidocaine, Etidronate Disodium, Etidronic Acid, Etifenin, Etintidine Hydrochloride, etizolam, Etodolac, Etofenamate, Etoformin Hydrochloride, Etomidate, Etonogestrel, Etoperidone Hydrochloride, Etoposide, Etoprine, Etoxadrol Hydrochloride, Etozolin, etrabamine, Etretinate, Etryptamine Acetate, Eucatropine Hydrochloride, Eugenol, Euprocin Hydrochloride, eveminomicin, Exametazime, examorelin, Exaprolol Hydrochloride, exemestane, fadrozole, faeriefungin, Famciclovir, Famotidine, Fampridine, fantofarone, Fantridone Hydrochloride, faropenem, fasidotril, fasudil, fazarabine, fedotozine, felbamate, Felbinac, Felodipine, Felypressin, Fenalamide, Fenamole, Fenbendazole, Fenbufen, Fencibutirol, Fenclofenac, Fenclonine, Fenclorac, Fendosal, Fenestrel, Fenethylline Hydrochloride, Fenfluramine Hydrochloride, Fengabine, Fenimide, Fenisorex, Fenmetozole Hydrochloride, Fenmetramide, Fenobam, Fenoctimine Sulfate, fenofibrate, fenoldopam, Fenoprofen, Fenoterol, Fenpipalone, Fenprinast Hydrochloride, Fenprostalene, Fenquizone, fenretinide, fenspiride, Fentanyl Citrate, Fentiazac, Fenticlor, fenticonazole, Fenyripol Hydrochloride, fepradinol, ferpifosate sodium, ferristene, ferrixan, Ferrous Sulfate, Dried, Ferumoxides, ferumoxsil, Fetoxylate Hydrochloride, fexofenadine, Fezolamine Fumarate, Fiacitabine, Fialuridine, Fibrinogen 1 125, filgrastim, Filipin, finasteride, Flavodilol Maleate, flavopiridol, Flavoxate Hydrochloride, Flazalone, flecainide, flerobuterol, Fleroxacin, flesinoxan, Flestolol Sulfate, Fletazepam, flezelastine, flobufen, Floctafenine, flomoxef, Flordipine, florfenicol, florifenine, flosatidil, Flosequinan, Floxacillin, Floxuridine, fluasterone, Fluazacort, Flubanilate Hydrochloride, Flubendazole, Flucindole, Flucloronide, Fluconazole, Flucytosine, Fludalanine, Fludarabine Phosphate, Fludazonium Chloride, Fludeoxyglucose F 18, Fludorex, Fludrocortisone Acetate, Flufenamic Acid, Flufenisal, Flumazenil, flumecinol, Flumequine, Flumeridone, Flumethasone, Flumetramide, Flumezapine, Fluminorex, Flumizole, Flumoxonide, flunarizine, Flunidazole, Flunisolide, Flunitrazepam, Flunixin, fluocalcitriol, Fluocinolone Acetonide, Fluocinonide, Fluocortin Butyl, Fluocortolone, Fluorescein, fluorodaunorunicin hydrochloride, Fluorodopa F 18, Fluorometholone, Fluorouracil, Fluotracen Hydrochloride, Fluoxetine, Fluoxymesterone, fluparoxan, Fluperamide, Fluperolone Acetate, Fluphenazine Decanoate, flupirtine, Fluprednisolone, Fluproquazone, Fluprostenol Sodium, Fluquazone, Fluradoline Hydrochloride, Flurandrenolide, Flurazepam Hydrochloride, Flurbiprofen, Fluretofen, flurithromycin, Flurocitabine, Flurofamide, Flurogestone Acetate, Flurothyl, Fluroxene, Fluspiperone, Fluspirilene, Fluticasone Propionate, flutrimazole, Flutroline, fluvastatin, Fluvastatin Sodium, fluvoxamine, Fluzinamide, Folic Acid, Follicle regulatory protein, Folliculostatin, Fomepizole, Fonazine Mesylate, forasartan, forfenimex, forfenirmex, formestane, Formocortal, formoterol, Fosarilate, Fosazepam, Foscarnet Sodium, fosfomycin, Fosfonet Sodium, fosinopril, Fosinoprilat, fosphenytoin, Fosquidone, Fostedil, fostriecin, fotemustine, Fuchsin, Basic, Fumoxicillin, Fungimycin, Furaprofen, Furazolidone, Furazolium Chloride, Furegrelate Sodium, Furobufen, Furodazole, Furosemide, Fusidate Sodium, Fusidic Acid, gabapentin, Gadobenate Dimeglumine, gadobenic acid, gadobutrol, Gadodiamide, gadolinium texaphyrin, Gadopentetate Dimegiumine, gadoteric acid, Gadoteridol, Gadoversetamide, galantamine, galdansetron, Galdansetron Hydrochloride, Gallamine Triethiodide, gallium nitrate, gallopamil, galocitabine, Gamfexine, gamolenic acid, Ganciclovir, ganirelix, gelatinase inhibitors, Gemcadiol, Gemcitabine, Gemeprost, Gemfibrozil, Gentamicin Sulfate, Gentian Violet, gepirone, Gestaclone, Gestodene, Gestonorone Caproate, Gestrinone, Gevotroline Hydrochloride, girisopam, glaspimod, glaucocalyxin A, Glemanserin, Gliamilide, Glibornuride, Glicetanile Sodium, Gliflumide, Glimepiride, Glipizide, Gloximonam, Glucagon, glutapyrone, glutathione inhibitors, Glutethimide, Glyburide, glycopine, glycopril, Glycopyrrolate, Glyhexamide, Glymidine Sodium, Glyoctamide, Glyparamide, Gold Au 198, Gonadoctrinins, Gonadorelin, Gonadotropins, Goserelin, Gramicidin, Granisetron, grepafloxacin, Griseofulvin, Guaiapate, Guaithylline, Guanabenz, Guanabenz Acetate, Guanadrel Sulfate, Guancydine, Guanethidine Monosulfate, Guanfacine Hydrochloride, Guanisoquin Sulfate, Guanoclor Sulfate, Guanoctine Hydrochloride, Guanoxabenz, Guanoxan Sulfate, Guanoxyfen Sulfate, Gusperimus Trihydrochloride, Halazepam, Halcinonide, halichondrin B, Halobetasol Propionate, halofantrine, Halofantrine Hydrochloride, Halofenate, Halofuginone Hydrobromide, halomon, Halopemide, Haloperidol, halopredone, Haloprogesterone, Haloprogin, Halothane, Halquinols, Hamycin, Han memopausal gonadotropins, hatomamicin, hatomarubigin A, hatomarubigin B, hatomarubigin C, hatomarubigin D, Heparin Sodium, hepsulfam, heregulin, Hetacillin, Heteronium Bromide, Hexachlorophene:Hydrogen Peroxide, Hexafluorenium Bromide, hexamethylene bisacetamide, Hexedine, Hexobendine, Hexoprenaline Sulfate, Hexylresorcinol, Histamine Phosphate, Histidine, Histoplasmin, Histrelin, Homatropine Hydrobromide, Hoquizil Hydrochloride, Human chorionic gonadotropin, Hycanthone, Hydralazine Hydrochloride, Hydralazine Polistirex, Hydrochlorothiazide, Hydrocodone Bitartrate, Hydrocortisone, Hydroflumethiazide, Hydromorphone Hydrochloride, Hydroxyamphetamine Hydrobromide, Hydroxychloroquine Sulfate, Hydroxyphenamate, Hydroxyprogesterone Caproate, Hydroxyurca, Hydroxyzine Hydrochloride, Hymecromone, Hyoscyamine, hypericin, Ibafloxacin, ibandronic acid, ibogaine, Ibopamine, ibudilast, Ibufenac, Ibuprofen, Ibutilide Fumarate, Icatibant Acetate, Ichthammol, Icotidine, idarubicin, idoxifene, Idoxuridine, idramantone, Iemefloxacin, Iesopitron, Ifetroban, Ifosfamide, Ilepeimide, illimaquinone, ilmofosine, ilomastat, Ilonidap, iloperidone, iloprost, Imafen Hydrochloride, Imazodan Hydrochloride, imidapril, imidazenil, imidazoacridones, Imidecyl Iodine, Imidocarb Hydrochloride, Imidoline Hydrochloride, Imidurea, Imiloxan Hydrochloride, Imipenem, Imipramine Hydrochloride, imiquimod, immunostimulant peptides, Impromidine Hydrochloride, Indacrinone, Indapamide, Indecainide Hydrochloride, Indeloxazine Hydrochloride, Indigotindisulfonate Sodium, indinavir, Indocyanine Green, Indolapril Hydrochloride, Indolidan, indometacin, Indomethacin Sodium, Indoprofen, indoramin, Indorenate Hydrochloride, Indoxole, Indriline Hydrochloride, inocoterone, inogatran, inolimomab, Inositol Niacinate, Insulin, interferons, interleukins, Intrazole, Intriptyline Hydrochloride, iobenguane, Iobenzamic Acid, iobitridol, Iocarmate Meglumine, Iocarmic Acid, Iocetamic Acid, Iodamide, Iodine, Iodipamide Meglumine, Iodixanol, iodoamiloride, Iodoantipyrine I 131, Iodocholesterol I 131, iododoxorubicin, Iodohippurate Sodium I 131, Iodopyracet I 125, Iodoquinol, Iodoxamate Meglumine, Iodoxamie Acid, Ioglicic Acid, Iofetamine Hydrochloride I 123, iofratol, Ioglucol, Ioglucomide, Ioglycamic Acid, Iogulamide, Iohexol, iomeprol, Iomethin I 125, Iopamidol, Iopanoic Acid, iopentol, Iophendylate, Ioprocemic Acid, iopromide, Iopronic Acid, Iopydol, Iopydone, iopyrol, Iosefamic Acid, Ioseric Acid, Iosulamide Meglumine, Iosumetic Acid, Iotasul, Iotetric Acid, Iothalamate Sodium, Iothalamic Acid, iotriside, Iotrolan, Iotroxic Acid, Iotyrosine 1 131, Ioversol, Ioxagiate Sodium, Ioxaglate Meglumine, Ioxaglic Acid, ioxilan, Ioxotrizoic Acid, ipazilide, ipenoxazone, ipidacrine, Ipodate Calcium, ipomeanol, 4-, Ipratropium Bromide, ipriflavone, Iprindole, Iprofenin, Ipronidazole, Iproplatin, Iproxamine Hydrochloride, ipsapirone, irbesartan, irinotecan, irloxacin, iroplact, irsogladine, Irtemazole, isalsteine, Isamoxole, isbogrel, Isepamicin, isobengazole, Isobutamben, Isocarboxazid, Isoconazole, Isoetharine, isofloxythepin, Isoflupredone Acetate, Isoflurane, Isoflurophate, isohomohalicondrin B, Isoleucine, Isomazole Hydrochloride, Isomylamine Hydrochloride, Isoniazid, Isopropamide Iodide, Isopropyl Alcohol, isopropyl unoprostone, Isoproterenol Hydrochloride, Isosorbide, Isosorbide Mononitrate, Isotiquimide, Isotretinoin, Isoxepac, Isoxicam, Isoxsuprine Hydrochloride, isradipine, itameline, itasetron, Itazigrel, itopride, Itraconazole, Ivermectin, jasplakinolide, Josamycin, kahalalide F, Kalafungin, Kanamycin Sulfate, Ketamine Hydrochloride, Ketanserin, Ketazocine, Ketazolam, Kethoxal, Ketipramine Fumarate, Ketoconazole, Ketoprofen, Ketorfanol, ketorolac, Ketotifen Fumarate, Kitasamycin, Labetalol Hydrochloride, Lacidipine, lacidipine, lactitol, lactivicin, laennec, lafutidine, lamellarin-N triacetate, lamifiban, Lamivudine, Lamotrigine, lanoconazole, Lanoxin, lanperisone, lanreotide, Lansoprazole, latanoprost, lateritin, laurocapram, Lauryl Isoquinolinium Bromide, Lavoltidine Succinate, lazabemide, Lecimibide, leinamycin, lemildipine, leminoprazole, lenercept, Leniquinsin, lenograstim, Lenperone, lentinan sulfate, leptin, leptolstatin, lercanidipine, Lergotrile, lerisetron, Letimide Hydrochloride, letrazuril, letrozole, Leucine, leucomyzin, Leuprolide Acetate, leuprolide+estrogen+progesterone, leuprorelin, Levamfetamine Succinate, levamisole, Levdobutamine Lactobionate, Leveromakalim, levetiracetam, Leveycloserine, levobetaxolol, levobunolol, levobupivacaine, levocabastine, levocarnitine, Levodopa, levodropropizine, levofloxacin, Levofuraltadone, Levoleucovorin Calcium, Levomethadyl Acetate, Levomethadyl Acetate Hydrochloride, levomoprolol, Levonantradol Hydrochloride, Levonordefrin, Levonorgestrel, Levopropoxyphene Napsylate, Levopropylcillin Potassium, levormeloxifene, Levorphanol Tartrate, levosimendan, levosulpiride, Levothyroxine Sodium, Levoxadrol Hydrochloride, Lexipafant, Lexithromycin, liarozole, Libenzapril, Lidamidine Hydrochloride, Lidocaine, Lidofenin, Lidoflazine, Lifarizine, Lifibrate, Lifibrol, Linarotene, Lincomycin, linear polyamine analogue, Linogliride, Linopirdine, linotroban, linsidomine, lintitript, lintopride, Liothyronine I 125, liothyronine sodium, Liotrix, lirexapride, lisinopril, lissoclinamide 7, Lixazinone Sulfate, lobaplatin, Lobenzarit Sodium, Lobucavir, Lodelaben, lodoxamide, Lofemizole Hydrochloride, Lofentanil Oxalate, Lofepramine Hydrochloride, Lofexidine Hydrochloride, lombricine, Lomefloxacin, lomerizine, Lometraline Hydrochloride, lometrexol, Lomofungin, Lomoxicam, Lomustine, Lonapalene, lonazolac, lonidamine, Loperamide Hydrochloride, loracarbef, Lorajmine Hydrochloride, loratadine, Lorazepam, Lorbamate, Lorcainide Hydrochloride, Loreclezole, Loreinadol, lorglumide, Lormetazepam, Lornoxicam, lornoxicam, Lortalamine, Lorzafone, losartan, losigamone, losoxantrone, Losulazine Hydrochloride, loteprednol, lovastatin, loviride, Loxapine, Loxoribine, lubeluzole, Lucanthone Hydrochloride, Lufironil, Lurosetron Mesylate, lurtotecan, luteinizing hormone, lutetium, Lutrelin Acetate, luzindole, Lyapolate Sodium, Lycetamine, lydicamycin, Lydimycin, Lynestrenol, Lypressin, Lysine, lysofylline, lysostaphin, lytic peptides, Maduramicin, Mafenide, magainin 2 amide, Magnesium Salicylate, Magnesium Sulfate, magnolol, maitansine, Malethamer, mallotochromene, mallotojaponin, Malotilate, malotilate, mangafodipir, manidipine, maniwamycin A, Mannitol, mannostatin A, manumycin E, manumycin F, mapinastine, Maprotiline, marimastat, Martek 8708, Martek 92211, Masoprocol, maspin, massetolide, matrilysin inhibitors, Maytansine, Mazapertine Succiniate, Mazindol, Mebendazole, Mebeverine Hydrochloride, Mebrofenin, Mebutamate, Mecamylamine Hydrochloride, Mechlorethamine Hydrochloride, Meclocycline, Meclofenamate Sodium, Mecloqualone, Meclorisone Dibutyrate, Medazepam Hydrochloride, Medorinone, Medrogestone, Medroxalol, Medroxyprogesterone, Medrysone, Meelizine Hydrochloride, Mefenamic Acid, Mefenidil, Mefenorex Hydrochloride, Mefexamide, Mefloquine Hydrochloride, Mefruside, Megalomicin Potassium Phosphate, Megestrol Acetate, Meglumine, Meglutol, Melengestrol Acetate, Melitracen Hydrochloride, Melphalan, Memotine Hydrochloride, Menabitan Hydrochloride, Menoctone, menogaril, Menotropins, Meobentine Sulfate, Mepartricin, Mepenzolate Bromide, Meperidine Hydrochloride, Mephentermine Sulfate, Mephenytoin, Mephobarbital, Mepivacaine Hydrochloride, Meprobamate, Meptazinol Hydrochloride, Mequidox, Meralein Sodium, merbarone, Mercaptopurine, Mercufenol Chloride, Mercury, Ammoniated, Merisoprol Hg 197, Meropenem, Mesalamine, Meseclazone, Mesoridazine, Mesterolone, Mestranol, Mesuprine Hydrochloride, Metalol Hydrochloride, Metaproterenol Polistirex, Metaraminol Bitartrate, Metaxalone, Meteneprost, meterelin, Metformin, Methacholine Chloride, Methacycline, Methadone Hydrochloride, Methadyl Acetate, Methalthiazide, Methamphetamine Hydrochloride, Methaqualone, Methazolamide, Methdilazine, Methenamine, Methenolone Acetate, Methetoin, Methicillin Sodium, Methimazole, methioninase, Methionine, Methisazone, Methixene Hydrochloride, Methocarbamol, Methohexital Sodium, Methopholine, Methotrexate, Methotrimeprazine, methoxatone, Methoxyflurane, Methsuximide, Methyclothiazide, Methyl Palmoxirate, Methylatropine Nitrate, Methylbenzethonium Chloride, Methyldopa, Methyldopate Hydrochloride, Methylene Blue, Methylergonovine Maleate, methylhistamine, R-alpha, methylinosine monophosphate, Methylphenidate Hydrochloride, Methylprednisolone, Methyltestosterone, Methynodiol Diacetate, Methysergide, Methysergide Maleate, Metiamide, Metiapine, Metioprim, metipamide, Metipranolol, Metizoline Hydrochloride, Metkephamid Acetate, metoclopramide, Metocurine Iodide, Metogest, Metolazone, Metopimazine, Metoprine, Metoprolol, Metoquizine, metrifonate, Metrizamide, Metrizoate Sodium, Metronidazole, Meturedepa, Metyrapone, Metyrosine, Mexiletine Hydrochloride, Mexrenoate Potassium, Mezlocillin, mfonelic Acid, Mianserin Hydrochloride, mibefradil, Mibefradil Dihydrochloridc, Mibolerone, michellamine B, Miconazole, microcolin A, Midaflur, Midazolam Hydrochloride, midodrine, mifepristone, Mifobate, miglitol, milacemide, milameline, mildronate, Milenperone, Milipertine, milnacipran, Milrinone, miltefosine, Mimbane Hydrochloride, minaprine, Minaxolone, Minocromil, Minocycline, Minoxidil, Mioflazine Hydrochloride, miokamycin, mipragoside, mirfentanil, mirimostim, Mirincamycin Hydrochloride, Mirisetron Maleate, Mirtazapine, mismatched double stranded RNA, Misonidazole, Misoprostol, Mitindomide, Mitocarcin, Mitocromin, Mitogillin, mitoguazone, mitolactol, Mitomalcin, Mitomycin, mitonafide, Mitosper, Mitotane, mitoxantrone, mivacurium chloride, mivazerol, mixanpril, Mixidine, mizolastine, mizoribine, Moclobemide, modafinil, Modaline Sulfate, Modecainide, moexipril, mofarotene, Mofegiline Hydrochloride, mofezolac, molgramostim, Molinazone, Molindone Hydrochloride, Molsidomine, mometasone, Monatepil Maleate, Monensin, Monoctanoin, Montelukast Sodium, montirelin, mopidamol, moracizine, Morantel Tartrate, Moricizine, Morniflumate, Morphine Sulfate, Morrhuate Sodium, mosapramine, mosapride, motilide, Motretinide, Moxalactam Disodium, Moxazocine, moxiraprine, Moxnidazole, moxonidine, Mumps Skin Test Antigen, mustard anticancer agent, Muzolimine, mycaperoxide B, Mycophenolic Acid, myriaporone, Nabazenil, Nabilone, Nabitan Hydrochloride, Naboctate Hydrochloride, Nabumetone, N-acetyldinaline, Nadide, nadifloxacin, Nadolol, nadroparin calcium, nafadotride, nafamostat, nafarelin, Nafcillin Sodium, Nafenopin, Nafimidone Hydrochloride, Naflocort, Nafomine Malate, Nafoxidine Hydrochloride, Nafronyl Oxalate, Naftifine Hydrochloride, naftopidil, naglivan, nagrestip, Nalbuphine Hydrochloride, Nalidixate Sodium, Nalidixic Acid, nalmefene, Nalmexone Hydrochloride, naloxone+pentazocine, Naltrexone, Namoxyrate, Nandrolone Phenpropionate, Nantradol Hydrochloride, Napactadine Hydrochloride, napadisilate, Napamezole Hydrochloride, napaviin, Naphazoline Hydrochloride, naphterpin, Naproxen, Naproxol, napsagatran, Naranol Hydrochloride, Narasin, naratriptan, nartograstim, nasaruplase, Natamycin, nateplase, Naxagolide Hydrochloride, Nebivolol, Nebramycin, nedaplatin, Nedocromil, Nefazodone Hydrochloride, Neflumozide Hydrochloride, Nefopam Hydrochloride, Nelezaprine Maleate, Nemazoline Hydrochloride, nemorubicin, Neomycin Palmitate, Neostigmine Bromide, neridronic acid, Netilmicin Sulfate, neutral endopeptidase, Neutramycin, Nevirapine, Nexeridine Hydrochloride, Niacin, Nibroxane, Nicardipine Hydrochloride, Nicergoline, Niclosamide, Nicorandil, Nicotinyl Alcohol, Nifedipine, Nifirmerone, Nifluridide, Nifuradene, Nifuraldezone, Nifuratel, Nifuratrone, Nifurdazil, Nifurimide, Nifurpirinol, Nifurquinazol, Nifurthiazole, nilutamide, Nilvadipine, Nimazone, Nimodipine, niperotidine, niravoline, Niridazole, nisamycin, Nisbuterol Mesylate, nisin, Nisobamate, Nisoldipine, Nisoxetine, Nisterime Acetate, Nitarsone, nitazoxanide, nitecapone, Nitrafudam Hydrochloride, Nitralamine Hydrochloride, Nitramisole Hydrochloride, Nitrazepam, Nitrendipine, Nitrocycline, Nitrodan, Nitrofurantoin, Nitrofurazone, Nitroglycerin, Nitromersol, Nitromide, Nitromifene Citrate, Nitrous Oxide, nitroxide antioxidant, nitrullyn, Nivazol, Nivimedone Sodium, Nizatidine, Noberastine, Nocodazole, Nogalamycin, Nolinium Bromide, Nomifensine Maleate, Noracymethadol Hydrochloride, Norbolethone, Norepinephrine Bitartrate, Norethindrone, Norethynodrel, Norfloxacin, Norflurane, Norgestimate, Norgestomet, Norgestrel, Nortriptyline Hydrochloride, Noscapine, Novobiocin Sodium, N-substituted benzaimides, Nufenoxole, Nylestriol, Nystatin, O6-benzylguanine, Obidoxime Chloride, Ocaperidone, Ocfentanil Hydrochloride, Ocinaplon, Octanoic Acid, Octazamide, Octenidine Hydrochloride, Octodrine, Octreotide, Octriptyline Phosphate, Ofloxacin, Ofornine, okicenone, Olanzapine, oligonucleotides, olopatadine, olprinone, olsalazine, Olsalazine Sodium, Olvanil, omeprazole, onapristone, ondansetron, Ontazolast, Oocyte maturation inhibitor, Opipramol Hydrochloride, oracin, Orconazole Nitrate, Orgotein, Orlislat, Ormaplatin, Ormetoprim, Ornidazole, Orpanoxin, Orphenadrine Citrate, osaterone, otenzepad, Oxacillin Sodium, Oxagrelate, oxaliplatin, Oxamarin Hydrochloride, oxamisole, Oxamniquine, oxandrolone, Oxantel Pamoate, Oxaprotiline Hydrochloride, Oxaprozin, Oxarbazole, Oxatomide, oxaunomycin, Oxazepam, oxcarbazepine, Oxendolone, Oxethazaine, Oxetorone Fumarate, Oxfendazole, Oxfenicine, Oxibendazole, oxiconazole, Oxidopamine, Oxidronic Acid, Oxifungin Hydrochloride, Oxilorphan, Oximonam, Oximonam Sodium, Oxiperomide, oxiracetam, Oxiramide, Oxisuran, Oxmetidine Hydrochloride, oxodipine, Oxogestone Phenpropionate, Oxolinic Acid, Oxprenolol Hydrochloride, Oxtriphylline, oxybutynin Chloride, Oxychlorosene, Oxycodone, Oxymetazoline Hydrochloride, Oxymetholone, Oxymorphone Hydrochloride, Oxypertine, Oxyphenbutazone, Oxypurinol, Oxytetracycline, Oxytocin, ozagrel, Ozolinone, Paclitaxel, palauamine, Paldimycin, palinavir, palmitoylrhizoxin, Palmoxirate Sodium, pamaqueside, Pamatolol Sulfate, pamicogrel, Pamidronate Disodium, pamidronic acid, Panadiplon, panamesine, panaxytriol, Pancopride, Pancuronium Bromide, panipenem, pannorin, panomifene, pantethine, pantoprazole, Papaverine Hydrochloride, parabactin, Parachlorophenol, Paraldehyde, Paramethasone Acetate, Paranyline Hydrochloride, Parapenzolate Bromide, Pararosaniline Pamoate, Parbendazole, Parconazole Hydrochloride, Paregoric, Pareptide Sulfate, Pargyline Hydrochloride, parnaparin sodium, Paromomycin Sulfate, Paroxetine, parthenolide, Partricin, Paulomycin, pazelliptine, Pazinaclone, Pazoxide, pazufloxacin, pefloxacin, pegaspargase, Pegorgotein, Pelanserin Hydrochloride, peldesine, Peliomycin, Pelretin, Pelrinone Hydrochloride, Pemedolac, Pemerid Nitrate, pemirolast, Pemoline, Penamecillin, Penbutolol Sulfate, Penciclovir, Penfluridol, Penicillin G Benzathine, Penicillin G Potassium, Penicillin G Procaine, Penicillin G Sodium, Penicillin V, Penicillin V Benzathine, Penicillin V Hydrabamine, Penicillin V Potassium, Pentabamate, Pentaerythritol Tetranitrate, pentafuside, pentamidine, pentamorphone, Pentamustine, Pentapiperium Methylsulfate, Pentazocine, Pentetic Acid, Pentiapine Maleate, pentigetide, Pentisomicin, Pentizidone Sodium, Pentobarbital, Pentomone, Pentopril, pentosan, pentostatin, Pentoxifylline, Pentrinitrol, pentrozole, Peplomycin Sulfate, Pepstatin, perflubron, perfofamide, Perfosfamide, pergolide, Perhexiline Maleate, perillyl alcohol, Perindopril, perindoprilat, Perlapine, Permethrin, perospirone, Perphenazine, Phenacemide, phenaridine, phenazinomycin, Phenazopyridine Hydrochloride, Phenbutazone Sodium Glycerate, Phencarbamide, Phencyclidine Hydrochloride, Phendimetrazine Tartrate, Phenelzine Sulfate, Phenmetrazine Hydrochloride, Phenobarbital, Phenoxybenzamine Hydrochloride, Phenprocoumon, phenserine, phensuccinal, Phensuximide, Phentermine, Phentermine Hydrochloride, phentolamine mesilate, Phentoxifylline, Phenyl Aminosalicylate, phenylacetate, Phenylalanine, phenylalanyl ketoconazole, Phenylbutazone, Phenylephrine Hydrochloride, Phenylpropanolamine Hydrochloride, Phenylpropanolamine Polistirex, Phenyramidol Hydrochloride, Phenytoin, phosphatase inhibitors, Physostigmine, picenadol, picibanil, Picotrin Diolamine, picroliv, picumeterol, pidotimod, Pifarnine, Pilocarpine, pilsicainide, pimagedine, Pimetine Hydrochloride, pimilprost, Pimobendan, Pimozide, Pinacidil, Pinadoline, Pindolol, pinnenol, pinocebrin, Pinoxepin Hydrochloride, pioglitazone, Pipamperone, Pipazethate, pipecuronium bromide, Piperacetazine, Piperacillin Sodium, Piperamide Maleate, Piperazine, Pipobroman, Piposulfan, Pipotiazine Palmitate, Pipoxolan Hydrochloride, Piprozolin, Piquindone Hydrochloride, Piquizil Hydrochloride, Piracetam, Pirandamine Hydrochloride, pirarubicin, Pirazmonam Sodium, Pirazolac, Pirbenicillin Sodium, Pirbuterol Acetate, Pirenperone, Pirenzepine Hydrochloride, piretanide, Pirfenidone, Piridicillin Sodium, Piridronate Sodium, Piriprost, piritrexim, Pirlimycin Hydrochloride, pirlindole, pirmagrel, Pirmenol Hydrochloride, Pirnabine, Piroctone, Pirodavir, pirodomast, Pirogliride Tartrate, Pirolate, Pirolazamide, Piroxantrone Hydrochloride, Piroxicam, Piroximone, Pirprofen, Pirquinozol, Pirsidomine, Prenylamine, Pituitary, Posterior, Pivampicillin Hydrochloride, Pivopril, Pizotyline, placetin A, platinum compounds, platinum-triamine complex, Plicamycin, Plomestane, Pobilukast Edamine, Podofilox, Poisonoak Extract, Poldine Methylsulfate, Poliglusam, Polignate Sodium, Polymyxin B Sulfate, Polythiazide, Ponalrestat, Porfimer Sodium, Porfiromycin, Potassium Chloride, Potassium Iodide, Potassium Permanganate, Povidone-Iodine, Practolol, Pralidoxime Chloride, Pramiracetam Hydrochloride, Pramoxine Hydrochloride, Pranolium Chloride, Pravadoline Maleate, Pravastatin (Pravachol), Prazepam, Prazosin, Prazosin Hydrochloride, Prednazate, Prednicarbate, Prednimustine, Prednisolone, Prednisone, Prednival, Pregnenolone Succiniate, Prenalterol Hydrochloride, Pridefine Hydrochloride, Prifelone, Prilocaine Hydrochloride, Prilosec, Primaquine Phosphate, Primidolol, Primidone, Prinivil, Prinomide Tromethamine, Prinoxodan, Prizidilol Hydrochloride, Proadifen Hydrochloride, Probenecid, Probicromil Calcium, Probucol, Procainamide Hydrochloride, Procaine Hydrochloride, Procarbazine Hydrochloride, Procaterol Hydrochloride, Prochlorperazine, Procinonide, Proclonol, Procyclidine Hydrochloride, Prodilidine Hydrochloride, Prodolic Acid, Profadol Hydrochloride, Progabide, Progesterone, Proglumide, Proinsulin Human, Proline, Prolintane Hydrochloride, Promazine Hydrochloride, Promethazine Hydrochloride, Propafenone Hydrochloride, propagermanium, Propanidid, Propantheline Bromide, Proparacaine Hydrochloride, Propatyl Nitrate, propentofylline, Propenzolate Hydrochloride, Propikacin, Propiomazine, Propionic Acid, propionylcarnitine, L-, propiram, propiram+paracetamol, propiverine, Propofol, Propoxycaine Hydrochloride, Propoxyphene Hydrochloride, Propranolol Hydrochloride, Propulsid, propyl bis-acridone, Propylhexedrine, Propyliodone, Propylthiouracil, Proquazone, Prorenoate Potassium, Proroxan Hydrochloride, Proscillaridin, Prostalene, prostratin, Protamine Sulfate, protegrin, Protirelin, protosufloxacin, Protriptyline Hydrochloride, Proxazole, Proxazole Citrate, Proxicromil, Proxorphan Tartrate, prulifloxacin, Pseudoephedrine Hydrochloride, Puromycin, purpurins, Pyrabrom, Pyrantel Pamoate, Pyrazinamide, Pyrazofurin, pyrazoloacridine, Pyridostigmine Bromide, Pyrilamine Maleate, Pyrimethamine, Pyrinoline, Pyrithione Sodium, Pyrithione Zinc, Pyrovalerone Hydrochloride, Pyroxamine Maleate, Pyrrocaine, Pyrroliphene Hydrochloride, Pyrrolnitrin, Pyrvinium Pamoate, Quadazocine Mesylate, Quazepam, Quazinone, Quazodine, Quazolast, quetiapine, quiflapon, quinagolide, Quinaldine Blue, quinapril, Quinaprilat, Quinazosin Hydrochloride, Quinbolone, Quinctolate, Quindecamine Acetate, Quindonium Bromide, Quinelorane Hydrochloride, Quinestrol, Quinfamide, Quingestanol Acetate, Quingestrone, Quinidine Gluconate, Quinielorane Hydrochloride, Quinine Sulfate, Quinpirole Hydrochloride, Quinterenol Sulfate, Quinuclium Bromide, Quinupristin, Quipazine Maleate, Rabeprazole Sodium, Racephenicol, Racepinephrine, raf antagonists, Rafoxanide, Ralitoline, raloxifene, raltitrexed, ramatroban, Ramipril, Ramoplanin, ramosetron, ranelic acid, Ranimycin, Ranitidine, ranolazine, Rauwolfia Serpentina, recainam, Recainam Hydrochloride, Reclazepam, regavirumab, Regramostim, Relaxin, Relomycin, Remacemide Hydrochloride, Remifentanil Hydrochloride, Remiprostol, Remoxipride, Repirinast, Repromicin, Reproterol Hydrochloride, Reserpine, resinferatoxin, Resorcinol, retelliptine demethylated, reticulon, reviparin sodium, revizinone, rhenium Re 186 etidronate, rhizoxin, Ribaminol, Ribavirin, Riboprine, ribozymes, ricasetron, Ridogrel, Rifabutin, Rifametane, Rifamexil, Rifamide, Rifampin, Rifapentine, Rifaximin, RII retinamide, rilopirox, Riluzole, rimantadine, Rimcazole Hydrochloride, Rimexolone, Rimiterol Hydrobromide, rimoprogin, riodipine, Rioprostil, Ripazepam, ripisartan, Risedronate Sodium, risedronic acid, Risocaine, Risotilide Hydrochloride, rispenzepine, Risperdal, Risperidone, Ritanserin, ritipenem, Ritodrine, Ritolukast, ritonavir, rizatriptan benzoate, Rocastine Hydrochloride, Rocuronium Bromide, Rodocaine, Roflurane, Rogletimide, rohitukine, rokitamycin, Roletamicide, Rolgamidine, Rolicyprine, Rolipram, Rolitetracycline, Rolodine, Romazarit, romurtide, Ronidazole, ropinirole, Ropitoin Hydrochloride, ropivacaine, Ropizine, roquinimex, Rosaramicin, Rosoxacin, Rotoxamine, roxaitidine, Roxarsone, roxindole, roxithromycin, rubiginone B1, ruboxyl, rufloxacin, rupatidine, Rutamycin, ruzadolane, Sabeluzole, safingol, safironil, saintopin, salbutamol, R-, Salcolex, Salethamide Maleate, Salicyl Alcohol, Salicylamide, Salicylate Meglumine, Salicylic Acid, Salmeterol, Salnacediin, Salsalate, sameridine, sampatrilat, Sancycline, sanfetrinem, Sanguinarium Chloride, Saperconazole, saprisartan, sapropterin, saquinavir, Sarafloxacin Hydrochloride, Saralasin Acetate, SarCNU, sarcophytol A, sargramostim, Sarmoxicillin, Sarpicillin, sarpogrelate, saruplase, saterinone, satigrel, satumomab pendetide, Schick Test Control, Scopafungin, Scopolamine Hydrobromide, Scrazaipine Hydrochloride, Sdi 1 mimetics, Secalciferol, Secobarbital, Seelzone, Seglitide Acetate, selegiline, Selegiline Hydrochloride, Selenium Sulfide, Selenomethionine Se 75, Selfotel, sematilide, semduramicin, semotiadil, semustine, sense oligonucleotides, Sepazonium Chloride, Seperidol Hydrochloride, Seprilose, Seproxetine Hydrochloride, Seractide Acetate, Sergolexole Maleate, Serine, Sermetacin, Sermorelin Acetate, sertaconazole, sertindole, sertraline, setiptiline, Setoperone, sevirumab, sevoflurane, sezolamide, Sibopirdine, Sibutramine Hydrochloride, signal transduction inhibitors, Silandrone, silipide, silteplase, Silver Nitrate, simendan, Simtrazene, Simvastatin, Sincalide, Sinefungin, sinitrodil, sinnabidol, sipatrigine, sirolimus, Sisomicin, Sitogluside, sizofiran, sobuzoxane, Sodium Amylosulfate, Sodium Iodide I 123, Sodium Nitroprusside, Sodium Oxybate, sodium phenylacetate, Sodium Salicylate, solverol, Solypertine Tartrate, Somalapor, Somantadine Hydrochloride, somatomedin B, somatomedin C, somatrem, somatropin, Somenopor, Somidobove, sonermin, Sorbinil, Sorivudine, sotalol, Soterenol Hydrochloride, Sparfloxacin, Sparfosate Sodium, sparfosic acid, Sparsomycin, Sparteine Sulfate, Spectinomycin Hydrochloride, spicamycin D, Spiperone, Spiradoline Mesylate, Spiramycin, Spirapril Hydrochloride, Spiraprilat, Spirogermanium Hydrochloride, Spiromustine, Spironolactone, Spiroplatin, Spiroxasone, splenopentin, spongistatin 1, Sprodiamide, squalamine, Stallimycin Hydrochloride, Stannous Pyrophosphate, Stannous Sulfur Colloid, Stanozolol, Statolon, staurosporine, stavudine, Steffimycin, Stenbolone Acetate, stepronin, Stilbazium Iodide, Stilonium Iodide, stipiamide, Stiripentol, stobadine, Streptomycin Sulfate, Streptonicozid, Streptonigrin, Streptozocin, stromelysin inhibitors, Strontium Chloride Sr 89, succibun, Succimer, Succinylcholine Chloride, Sucralfate, Sucrosofate Potassium, Sudoxicam, Sufentanil, Sufotidine, Sulazepam, Sulbactam Pivoxil, Sulconazole Nitrate, Sulfabenz, Sulfabenzamide, Sulfacetamide, Sulfacytine, Sulfadiazine, Sulfadoxine, Sulfalene, Sulfamerazine, Sulfameter, Sulfamethazine, Sulfamethizole, Sulfamethoxazole, Sulfamonomethoxine, Sulfamoxole, Sulfanilate Zinc, Sulfanitran, sulfasalazine, Sulfasomizole, Sulfazamet, Sulfinalol Hydrochloride, sulfinosine, Sulfinpyrazone, Sulfisoxazole, Sulfomyxin, Sulfonterol Hydrochloride, sulfoxamine, Sulinldac, Sulmarin, Sulnidazole, Suloctidil, Sulofenur, sulopenem, Suloxifen Oxalate, Sulpiride, Sulprostone, sultamicillin, Sulthiame, sultopride, sulukast, Sumarotene, sumatriptan, Suncillin Sodium, Suproclone, Suprofen, suradista, suramin, Surfomer, Suricainide Maleate, Suritozole, Suronacrine Maleate, Suxemerid Sulfate, swainsonine, symakalim, Symclosene, Symetine Hydrochloride, synthetic glycosaminoglycans, Taciamine Hydrochloride, Tacrine Hydrochloride, Tacrolimus, Talampicillin Hydrochloride, Taleranol, Talisomycin, tallimustine, Talmetacin, Talniflumate, Talopram Hydrochloride, Talosalate, Tametraline Hydrochloride, Tamoxifen, Tampramine Fumarate, Tamsulosin Hydrochloride, Tandamine Hydrochloride, tandospirone, tapgen, taprostene, Tasosartan, tauromustine, Taxane, Taxoid, Tazadolene Succinate, tazanolast, tazarotene, Tazifylline Hydrochloride, Tazobactam, Tazofelone, Tazolol Hydrochloride, Tebufelone, Tebuquine, Technetium Tc 99 m Bicisate, Teclozan, Tecogalan Sodium, Teecleukin, Teflurane, Tegafur, Tegretol, Teicoplanin, telenzepine, tellurapyrylium, telmesteine, telmisartan, telomerase inhibitors, Teloxantrone Hydrochloride, Teludipine Hydrochloride, Temafloxacin Hydrochloride, Tematropium Methyl sulfate, Temazepam, Temelastine, temocapril, Temocillin, temoporfin, temozolomide, Tenidap, Teniposide, tenosal, tenoxicam, tepirindole, Tepoxalin, Teprotide, terazosin, Terbinafine, Terbutaline Sulfate, Terconazole, terfenadine, terflavoxate, terguride, Teriparatide Acetate, terlakiren, terlipressin, terodiline, Teroxalene Hydrochloride, Teroxirone, tertatolol, Tesicam, Tesimide, Testolactone, Testosterone, Tetracaine, tetrachlorodecaoxide, Tetracycline, Tetrahydrozoline Hydrochloride, Tetramisole Hydrochloride, Tetrazolast Meglumine, tetrazomine, Tetrofosmin, Tetroquinone, Tetroxoprim, Tetrydamine, thaliblastine, Thalidomide, Theofibrate, Theophylline, Thiabendazole, Thiamiprine, Thiamphenicol, Thiamylal, Thiazesim Hydrochloride, Thiazinamium Chloride, Thiethylperazine, Thimerfonate Sodium, Thimerosal, thiocoraline, thiofedrine, Thioguanine, thiomarinol, Thiopental Sodium, thioperamide, Thioridazine, Thiotepa, Thiothixene, Thiphenamil Hydrochloride, Thiphencillin Potassium, Thiram, Thozalinone, Threonine, Thrombin, thrombopoietin, thrombopoietin mimetic, thymalfasin, thymopoietin receptor agonist, thymotrinan, Thyromedan Hydrochloride, Thyroxine 1 125, Thyroxine 1 131, Tiacrilast, Tiacrilast Sodium, tiagabine, Tiamenidine, tianeptine, tiapafant, Tiapamil Hydrochloride, Tiaramide Hydrochloride, Tiazofurin, Tibenelast Sodium, Tibolone, Tibric Acid, Ticabesone Propionate, Ticarbodine, Ticarcillin Cresyl Sodium, Ticlatone, ticlopidine, Ticrynafen, tienoxolol, Tifurac Sodium, Tigemonam Dicholine, Tigestol, Tiletamine Hydrochloride, Tilidine Hydrochloride, tilisolol, tilnoprofen arbamel, Tilorone Hydrochloride, Tiludronate Disodium, tiludronic acid, Timefurone, Timobesone Acetate, Timolol, tin ethyl etiopurpurin, Tinabinol, Tinidazole, Tinzaparin Sodium, Tioconazole, Tiodazosin, Tiodonium Chloride, Tioperidone Hydrochloride, Tiopinac, Tiospirone Hydrochloride, Tiotidine, tiotropium bromide, Tioxidazole, Tipentosin Hydrochloride, Tipredane, Tiprenolol Hydrochloride, Tiprinast Meglumine, Tipropidil Hydrochloride, Tiqueside, Tiquinamide Hydrochloride, tirandalydigin, Tirapazamine, tirilazad, tirofiban, tiropramide, titanocene dichloride, Tixanox, Tixocortol Pivalate, Tizanidine Hydrochloride, Tobramycin, Tocainide, Tocamphyl, Tofenacin Hydrochloride, Tolamolol, Tolazamide, Tolazoline Hydrochloride, Tolbutamide, Tolcapone, Tolciclate, Tolfamide, Tolgabide, lamotrigine, Tolimidone, Tolindate, Tolmetin, Tolnaftate, Tolpovidone 1 131, Tolpyrramide, Tolrestat, Tomelukast, Tomoxetine Hydrochloride, Tonazocine Mesylate, Topiramate, topotecan, Topotecan Hydrochloride, topsentin, Topterone, Toquizine, torasemide, toremifene, Torsemide, Tosifen, Tosufloxacin, totipotent stem cell factor, Tracazolate, trafermin, Tralonide, Tramadol Hydrochloride, Tramazoline Hydrochloride, trandolapril, Tranexamic Acid, Tranilast, Transcainide, translation inhibitors, traxanox, Trazodone Hydrochloride, Trazodone-HCL, Trebenzomine Hydrochloride, Trefentanil Hydrochloride, Treloxinate, Trepipam Maleate, Trestolone Acetate, tretinoin, Triacetin, triacetyluridine, Triafungin, Triamcinolone, Triampyzine Sulfate, Triamterene, Triazolam, Tribenoside, tricaprilin, Tricetamide, Trichlormethiazide, trichohyalin, triciribine, Tricitrates, Triclofenol Piperazine, Triclofos Sodium, Triclonide, trientine, Trifenagrel, triflavin, Triflocin, Triflubazam, Triflumidate, Trifluoperazine Hydrochloride, Trifluperidol, Triflupromazine, Triflupromazine Hydrochloride, Trifluridine, Trihexyphenidyl Hydrochloride, Trilostane, Trimazosin Hydrochloride, trimegestone, Trimeprazine Tartrate, Trimethadione, Trimethaphan Camsylate, Trimethobenzamide Hydrochloride, Trimethoprim, Trimetozine, Trimetrexate, Trimipramine, Trimoprostil, Trimoxamine Hydrochloride, Triolein 1 125, Triolein 1 131, Trioxifene Mesylate, Tripamide, Tripelennamine Hydrochloride, Triprolidine Hydrochloride, Triptorelin, Trisulfapyrimidines, Troclosene Potassium, troglitazone, Trolamine, Troleandomycin, trombodipine, trometamol, Tropanserin Hydrochloride, Tropicamide, tropine ester, tropisetron, trospectomycin, trovafloxacin, trovirdine, Tryptophan, Tuberculin, Tubocurarine Chloride, Tubulozole Hydrochloride, tucarcsol, tulobuterol, turosteride, Tybamate, tylogenin, Tyropanoate Sodium, Tyrosine, Tyrothricin, tyrphostins, ubenimex, Uldazepam, Undecylenic Acid, Uracil Mustard, urapidil, Urea, Uredepa, uridine triphosphate, Urofollitropin, Urokinase, Ursodiol, valaciclovir, Valine, Valnoctamide, Valproate Sodium, Valproic Acid, valsartan, vamicamide, vanadeine, Vancomycin, vaninolol, Vapiprost Hydrochloride, Vapreotide, variolin B, Vasopressin, Vecuronium Bromide, velaresol, Velnacrine Maleate, venlafaxine, Veradoline Hydrochloride, veramine, Verapamil Hydrochloride, verdins, Verilopam Hydrochloride, Verlukast, Verofylline, veroxan, verteporfin, Vesnarinone, vexibinol, Vidarabine, vigabatrin, Viloxazine Hydrochloride, Vinblastine Sulfate, vinburnine citrate, Vincofos, vinconate, Vincristine Sulfate, Vindesine, Vindesine Sulfate, Vinepidine Sulfate, Vinglycinate Sulfate, Vinleurosine Sulfate, vinorelbine, vinpocetine, vintoperol, vinxaltine, Vinzolidine Sulfate, Viprostol, Virginiamycin, Viridofulvin, Viroxime, vitaxin, Volazocine, voriconazole, vorozole, voxergolide, Warfarin Sodium, Xamoterol, Xanomeline, Xanoxate Sodium, Xanthinol Niacinate, xemilofiban, Xenalipin, Xenbucin, Xilobam, ximoprofen, Xipamide, Xorphanol Mesylate, Xylamidine Tosylate, Xylazine Hydrochloride, Xylometazoline Hydrochloride, Xylose, yangambin, zabicipril, zacopride, zafirlukast, Zalcitabine, zaleplon, zalospirone, Zaltidine Hydrochloride, zaltoprofen, zanamivir, zankiren, zanoterone, Zantac, Zarirlukast, zatebradine, zatosetron, Zatosetron Maleate, zenarestat, Zenazocine Mesylate, Zeniplatin, Zeranol, Zidometacin, Zidovudine, zifrosilone, Zilantel, zilascorb, zileuton, Zimeldine Hydrochloride, Zinc Undecylenate, Zindotrine, Zinoconazole Hydrochloride, Zinostatin, Zinterol Hydrochloride, Zinviroxime, ziprasidone, Zobolt, Zofenopril Calcium, Zofenoprilat, Zolamine Hydrochloride, Zolazepam Hydrochloride, zoledronie acid, Zolertine Hydrochloride, zolmitriptan, zolpidem, Zomepirac Sodium, Zometapine, Zoniclezole Hydrochloride, Zonisamide, zopiclone, Zopolrestat, Zorbamyciin, Zorubicin Hydrochloride, zotepine, Zucapsaicin or its pharmaceutically acceptable salts thereof.

As indicated above this portion may comprise auxiliary excipients such as for example diluents, binders, lubricants, surfactants, disintegrants, plasticisers, anti-tack agents, opacifying agents, pigments, and such like. As will be appreciated by those skilled in the art, the exact choice of excipient and their relative amounts will depend to some extent on the final oral dosage form.

Suitable diluents include for example pharmaceutically acceptable inert fillers such as microcrystalline cellulose, lactose, starch, dibasic calcium phosphate, saccharides, and/or mixtures of the foregoing. Examples of diluents include microcrystalline celluloses such as those sold under the Trade Mark Avicel PH 101, Avicel PH 102, Avicel PH 112, Avicel PH 200, Avicel PH301 and Avicel PH 302; lactose such as lactose monohydrate, lactose anhydrous and Pharmatose DCL21 (Pharmatose is a Trade Mark), including anhydrous, monohydrate and spray dried forms; dibasic calcium phosphate such as Emcompress (Emcompress is a Trade Mark); mannitol; Pearlitol SD 200 (Pearlitol SD 200 is a trade mark); starch; sorbitol; sucrose; and glucose.

Suitable binders include for example starch, povidone, hydroxypropylmethylcellulose, pregelatinised starch, hydroxypropylcellulose and/or mixtures of the foregoing.

Suitable lubricants, including agents that act on the flowability of the powder to be compressed are, for example, colloidal slilcon dioxide such as Aerosil 200 (Aerosil is a Trade Mark); talc; stearic acid, magnesium stearate, calcium stearate and sodium stearyl fumarate.

Suitable disintegrants include for example lightly crosslinked polyvinyl pyrrolidone, corn starch, potato starch, maize starch and modified starches, croscarmellose sodium, cross-povidone, sodium starch glycolate and combinations and mixtures thereof.

The amount of release controlling agent(s) to be used in will be determined based on drug release rate etc.

The release controlling agents(s) are selected from alkyl celluloses, hydroxyalkyl celluloses, cellulose ethers, cellulose esters, nitro celluloses, polymers of acrylic and methacrylic acids and esters thereof, polyamides, polycarbonates, polyalkylenes, polyalkylene glycols, polyalkylene terephthalates, polyvinyl esters, polyvinylpyrrolidone, polyglycolides, polysiloxanes and polyurethanes and co-polymers thereof.

The high water soluble/permeable release controlling agents is suitably polyvinyl alcohol, polyvinylpyrrolidone, methylcellulose, hydroxypropylcellulose, hydroxypropylmethyl cellulose or polyethylene glycol, alginates, polyacrylic acids, xanthun gum or a mixture thereof.

The ammonio methacrylatye copolymers are preferably selected from the group consisting of poly(ethyl acrylate, methyl methacrylate, trimethylammonioethyl methacrylate chloride) 1:2:0.1; poly(ethyl acrylate, methyl methacrylate, trimethylamonioethyl methacrylate chloride) 1:2:0.2 and poly(ethyl acrylate, methyl methacrylate) 2:1

The low water soluble/permeable release controlling agents is suitably ethylcellulose, cellulose acetate, cellulose propionate (lower, medium or higher molecular weight), cellulose acetate propionate, cellulose acetate butyrate, cellulose acetate phthalate, cellulose triacetate, poly(methyl methacrylate), poly(ethyl methacrylate), poly(butyl methacrylate), poly(isobutyl methacrylate), and poly(hexyl methacrylate). Poly(isodecyl methacrylate), poly(lauryl methacrylate), poly (phenyl methacrylate), poly(methyl acrylate), poly (isopropyl acrylate), poly(isobutyl actylate), poly(octadecyl acrylate), waxes such as beeswax, carnauba wax, microcrystalline wax, and ozokerite; fatty alcohols such as cetostearyl alcohol, stearyl alcohol; cetyl alcohol and myristyl alcohol; and fatty acid esters such as glyceryl monostearate, glyceryl distearate, glycerol monooleate, acetylated monoglycerides, tristearin, tripalmitin, cetyl esters wax, glyceryl palmitostearate, glyceryl behenate, and hydrogenated castor oil or a mixture thereof.

The non-biodegradable materials are selected from but are not limited to Ammonio methacrylate copolymers type A and B as described in USP, Polyacrylate dispersion 30% as described in Ph. Eur., Polyvinyl acetate dispersion, cellulose derivatives such as ethylcellulose, cellulose acetate waxes such as beeswax, carnauba wax, microcrystalline wax, and ozokerite; fatty alcohols such as cetostearyl alcohol, stearyl alcohol; cetyl alcohol and myristyl alcohol; and fatty acid esters such as glyceryl monostearate, glyceryl distearate, glycerol monooleate, acetylated monoglycerides, tristearin, tripalmitin, cetyl esters wax, glyceryl palmitostearate, glyceryl behenate, and hydrogenated castor oil.

The mucoadhesive release controlling agents are selected from but are not limited to carbopol, sodium carboxymethyl cellulose, hydroxypropyl cellulose, hydroxypropylmethyl cellulose, hydroxyethyl cellulose, methyl cellulose, sodium hyaluronate, gaur gum, sodium alginate, polycabophil, starch, dextran or chitosan.

Active ingredients especially the poorly soluble active ingredients mentioned above can be micronized to increase solubility and/or bioavialabiity.

The novel modified release dosage form of the present invention can be manufactured by the following procedure: The micro matrix particles can be manufactured in accordance with usual techniques in which the active ingredient and one or more hydrophobic release controlling agents are mixed and granulated by adding solvent in a low or high shear mixer or by fluidized bed granulator. The granulate is dried, preferably in a fluidized bed dryer. The dried granulate is sized. The sizing of the micromatrix particles can be done using oscillating granulator, comminuting mill or any other conventional method. The sieve used for the sizing can have openings from 0.25 mm to 5 mm. Alternatively the micro matrix particles can be made by extrusion, spheronization or by roller compaction. The micro matrix particles can be coated by a solution of one or more hydrophobic release controlling agents by any known method, including spray application. Spraying can be carried out using a fluidized bed coated (preferably Wurster coating), or in a pan coating system. Alternatively the coating of the micro matrix particles with one or more rate controlling agents can be done by hot melt process using a granulator or fluidized bed coated (preferably Wurster coating), or in a pan coating system. The compression of tablets is carried out on usual compression machines (e.g. machines of the Manesty, Cadmach or Kilian) The tablets can be made of various sizes and shapes.

Process for manufacturing combination dosage form as per instant invention comprising highly soluble drug as modified release and another active ingredient as immediate release or modified release:

Part (A)—Granules comprising highly soluble drug: as described above.

Part (B)—It may have following options for manufacturing of formulation for another active ingredient.

i) Granules for multilayered or compression coated tablets—It be manufactured in accordance with usual techniques in which the active ingredient(s) and other excipients are mixed and granulated by adding solution of binder in a low or high shear mixer or by fluidized bed granulation. The granulate is dried, preferably in a fluidized bed dryer. The dried granulate is sieved and mixed with lubricants and disintegrants. Alternatively the manufacture of granules of inner portion can be made by direct mixing of the directly compressible excipients or by roller compaction.

ii) Solution or suspension of active ingredient(s) for drug layering on compact part—Active ingredient(s) can be dissolved or suspended in solution of suitable binder(s). This solution or suspension can be sprayed or layered over the dosage form prepared as per the invention. Spraying can be carried out using a fluidized bed coated, or in a pan coating system.

C) Tablet Compression

Suitable tablet presses can be used for single layered tablets, multilayered tablets or compression coated tablets using granules prepared in part A and part B.

D) Capsule Filling

Compact tablets of highly soluble active ingredient and tablets or granules of another active ingredient can be filled in hard gelatin capsule shells by using suitable machines.

BRIEF DESCRIPTION OF THE DRAWINGS

FIG. 1 (b) is a cross section of coated micro matrix particles prepared by granulation and coating for the purpose of illustration only.

FIGS. 1 (a) and 1(b) show the cross section of the coated micro matrix particles 1 as described in the present invention and having a high solubility active ingredient 2, hydrophobic release controlling agent 3 and a coating of hydrophobic release controlling agent 4. FIGS. 2 and 3 show release of high solubility active agent 5 & 6 and 9 & 10 as per example 1 & 2 respectively from a dosage form prepared using dual retard technique and release of high solubility active agent 7 & 8 and 11 & 12 as per example 3 & 4 respectively from a dosage form prepared without using dual retard release technique. The total quantity of the hydrophobic release controlling agent is same in all the dosage forms inspite of that the figures clearly shows that dual retard technology significantly reduces the burst effect and effectively controls the release rate of the high solubility active ingredient for prolonged period. FIG. 4 shows release of high solubility active agent 13 & 14 as per example 8 from a dosage form prepared using dual retard technique and release of high solubility active agent 15 & 16 as per example 11 from a dosage form prepared without using dual retard release technique. The total quantity of the hydrophobic release controlling agent is same in all the dosage forms. In spite of that the figures clearly show that dual retard technology significantly reduces the burst effect and effectively controls the release rate of the high solubility antidiabetic active ingredient for prolonged period.

DESCRIPTION OF PREFERRED EMBODIMENTS

Figure 1A:
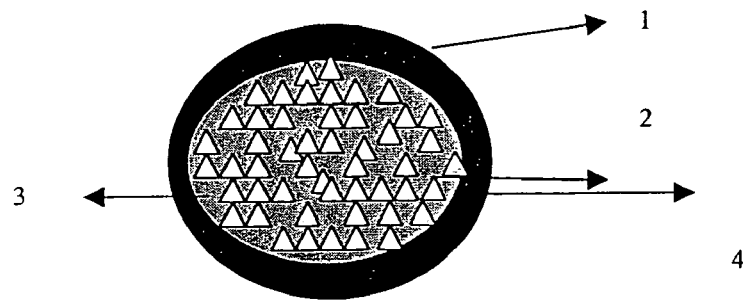
FIG. 1 (a) is a cross section of coated micro matrix particles prepared by spheronization and coating for the purpose of illustration only.
Figure 1B:
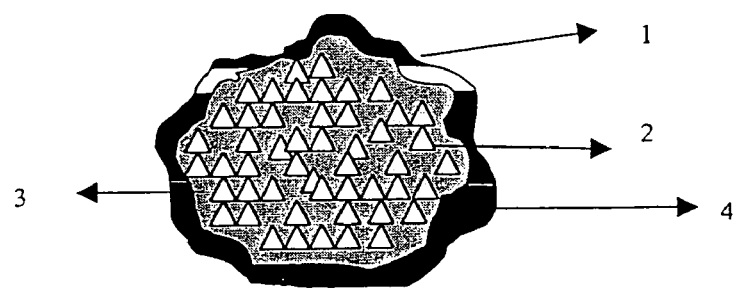
Figure 2:
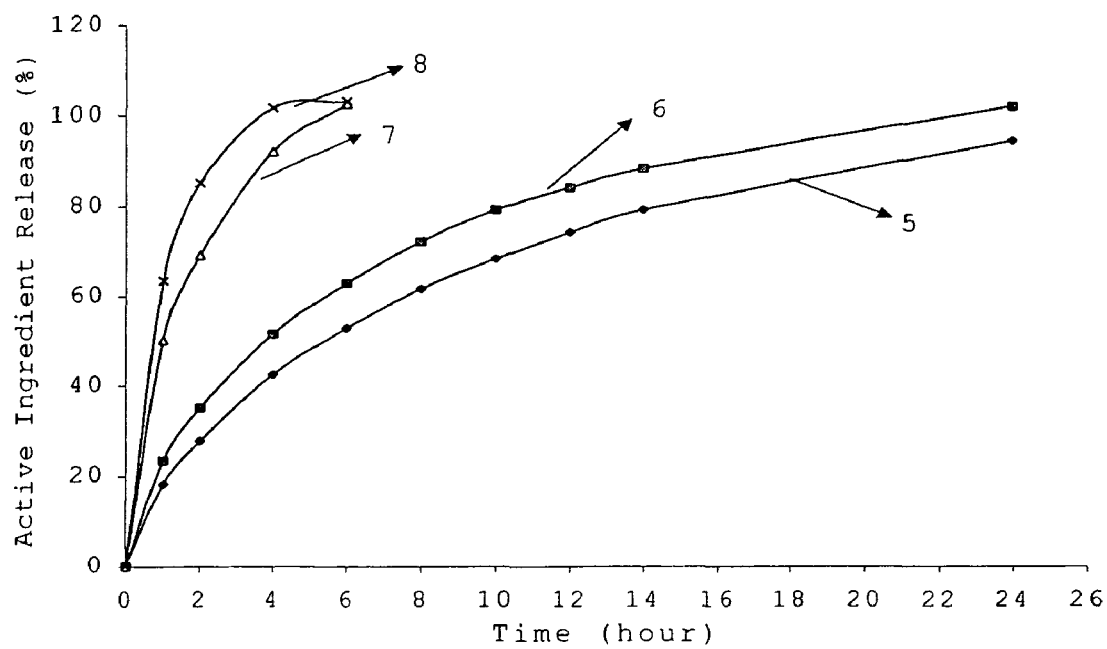
FIG. 2 is a plot of % active ingredient versus time for modified release active agent prepared using dual retard technique as described in the present invention and prepared without retard release technique as per examples 1 and 3.
Figure 3:
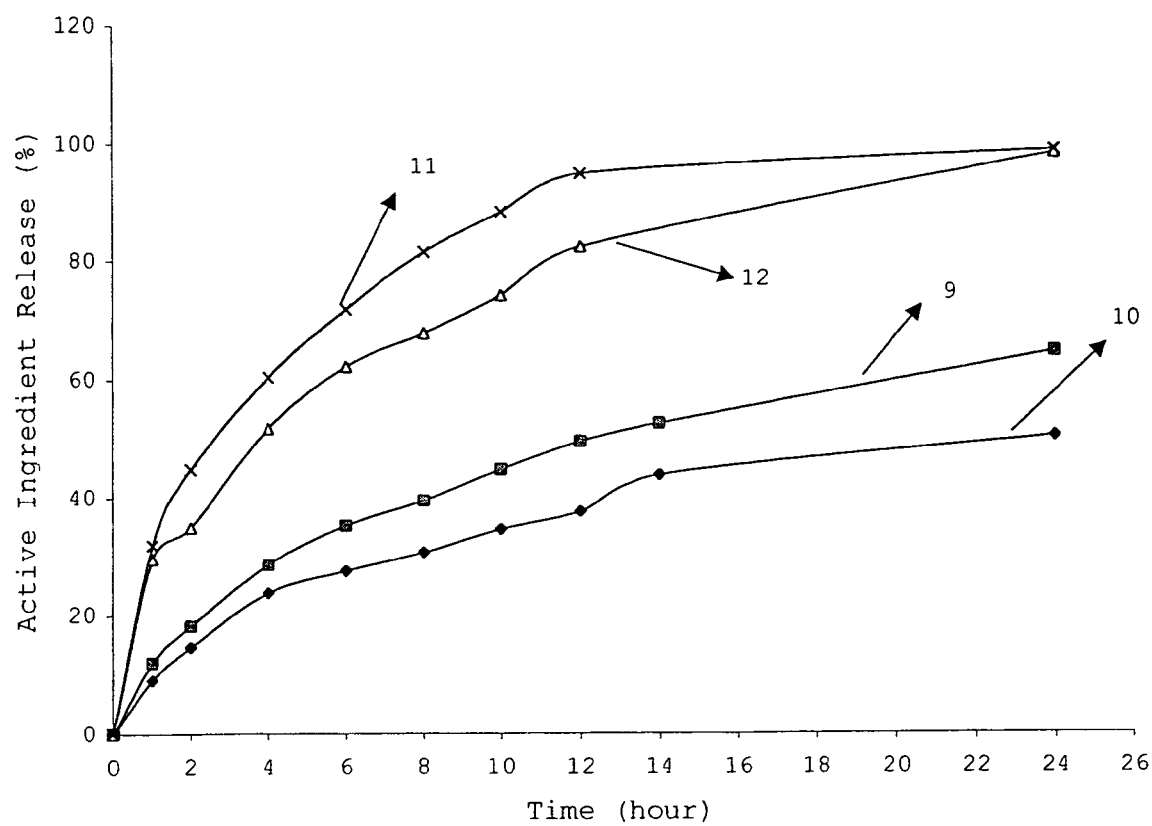
FIG. 3 is a plot of % active ingredient versus time for modified release active agent prepared using dual retard technique as described in the present invention and prepared without retard release technique as per examples 2 and 4.
Figure 4:
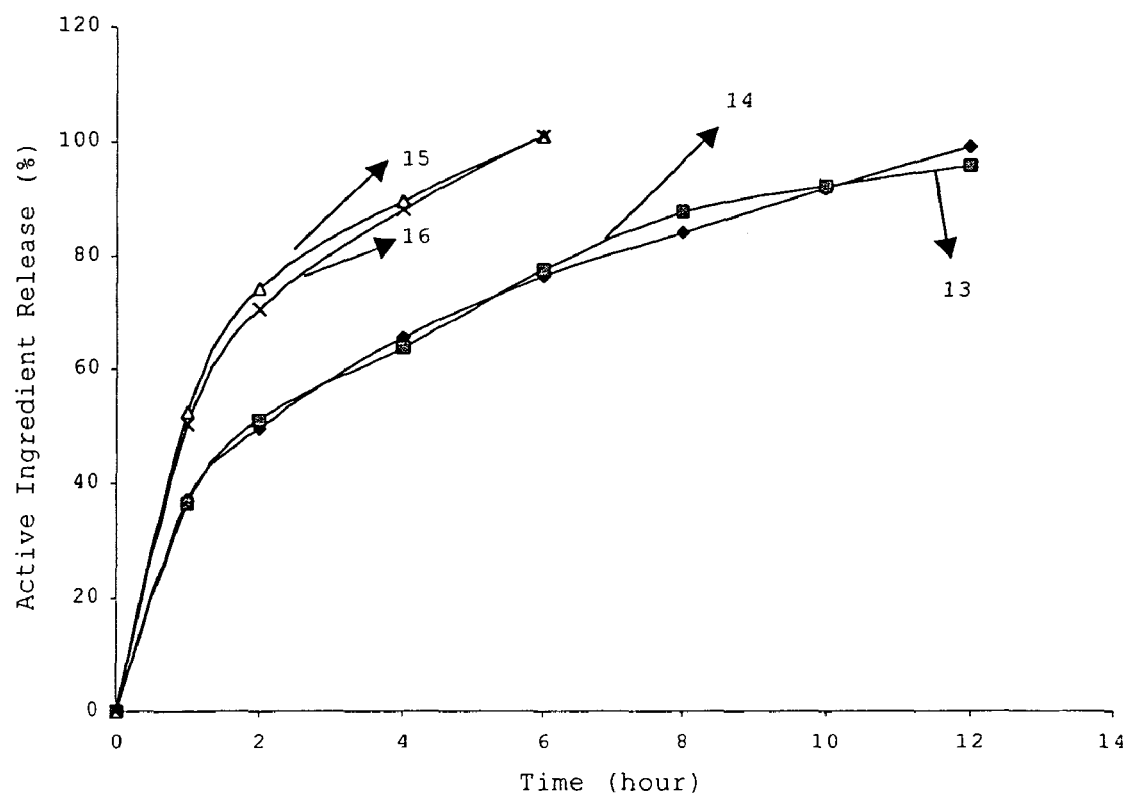
FIG. 4 is a plot of % active ingredient versus time for modified release active agent prepared using dual retard technique as described in the present invention and prepared without retard release technique as per examples 8 and 11 respectively.

The following examples further illustrate but by no means limit the present invention.

The dissolution of novel dosage form of the present invention was determined by following method.

| For sodium valproate- | |
| --- | --- |
| Instrument | Apparatus I, USP (basket) |
| Revolution | 60/min. |
| Temperature | 37 ± 0.5° C. |
| Dissolution medium | 1000 ml pH 6.8 buffer |
| For niacin- | |
| Instrument | Apparatus I, USP (Basket) |
| Revolution | 100/min. |
| Temperature | 37 ± 0.5° C. |
| Dissolution medium | 900 ml 0.1 N HCl |
| For venlafaxine hydrochloride- | |
| Instrument | Apparatus II, USP (Paddle) |
| Revolution | 100/min. |
| Temperature | 37 ± 0.5° C. |
| Dissolution medium | 500 ml water |

| For metformin hydrochloride- | |
| --- | --- |
| Instrument | Apparatus II, USP (Paddle) |
| Revolution | 50/min. |
| Temperature | 37 ± 0.5° C. |
| Dissolution medium | 900 ml 0.1 N HCl |

The dissolution of high solubility ingredient of the formulation of the present invention is achieved not more than 50% in 1 hour and from 25 to 90% in six hours.

The dissolution of metformin hydrochloride is achieved not more than 50% in 1 hour, and from 30 to 90% is in four hours and not less than 65% in 12 hours.

After oral administration of a dosage form of the present invention the maximum plasma concentration can be achieved between 700 ng/ml and 2500 ng/ml, preferably from 900 ng/ml to 2400 ng/ml and more preferably from 1000 ng/ml to 2350 ng/ml. The invivo mean dissolution time (MDT) of the dosage form of the present invention is approximately 4 to 6 hours. The minimum plasma concentration (at 24 hours) of the said dosage form ranges between 0 and 450 ng/ml after oral administration.

Conclusion:

The composition of the micromatrix particles and coated micromatrix particles of the dosage form comprising niacin is as follows:

| Micromatrix particles- | |
| --- | --- |
| Niacin | 75% w/w to 49% w/w |
| EUDRAGIT RS (Ammonio Methacrylate Copolymer type B USP) | 1% w/w to 25 w/w |
| Coated micro matrix particles | |
| Micro matrix particles | 70% w/w to 99% w/w |
| Hydrogenated castor oil | 1% w/w to 30% w/w |
| Magnesium stearate | 0% w/w to 2% w/w |

The composition of the micromatrix particles and coated micromatrix particles of the dosage form comprising metformin hydrochloride is as follows:

| Micromatrix particles- | |
| --- | --- |
| Methformin hydrochloride | 75% w/w to 49% w/w |
| EUDRAGIT RS (Ammonio Methacrylate Copolymer type B USP) | 1% w/w to 25 w/w |
| Coated micro matrix particles | |
| Micro matrix particles | 70% w/w to 99% w/w |
| Hydrogenated castor oil | 1% w/w to 30% w/w |
| Magnesium Stearate | 0% w/w to 2% w/w |

Description of Preferred Embodiments

Examples

Example 1

A) Micro matrix particles—90.91% w/w of sodium valproate is mixed with 9.09% w/w of Eudragit RS (Ammonio Methacrylate Copolymer type B USP) and the mixture is granulated with a solvent mixture of acetone and methylene chloride and then dried. The granules are sized.

B) Coating of Micro matrix particles—85.54% w/w of micro matrix particles is charged in fluidized bed processor. 13.61% w/w of hydrogenated castor oil is dissolved in acetone and this coating solution is sprayed to coat the micro matrix particles. The coated micro matrix particles are sieved and mixed with 0.86% w/w magnesium stearate.

C) Compression of Tablets

Tablet (1)—1286 mg granules are pressed to tablet (equivalent to 1000 mg sodium valproate) using 20.3×9.8 mm oval punches.

Tablet (2)—643 mg granules are pressed to tablet (equivalent to 500 mg sodium valproate) using 14.95×8.35 mm oblong punches.

The dissolution rate of the novel dosage form was determined (Table 1)

TABLE 1

Dissolution profile

% Released

|    | Tablet (1) | Tablet (2) |
|----|------------|------------|
| 1  | 18.2       | 23.4       |
| 2  | 27.8       | 35.1       |
| 4  | 42.5       | 51.5       |
| 6  | 52.8       | 62.9       |
| 8  | 61.6       | 72.1       |
| 10 | 68.3       | 79.2       |
| 12 | 74.2       | 84.1       |
| 14 | 79.2       | 88.3       |
| 24 | 94.4       | 102.0      |

Example 2

A) Micro matrix particles—90.91% w/w of niacin is mixed with 9.09% w/w of Eudragit RS (Ammonio Methacrylate Copolymer type B USP) and the mixture is granulated with a solvent mixture of acetone and methylene chloride and then dried. The granules are sized.

B) Coating of Micro matrix particles—85.54% w/w of micro matrix particles is charged in fluidized bed processor. 13.61% w/w of hydrogenated castor oil is dissolved in acetone and this coating solution is sprayed to coat the micro matrix particles. The coated micro matrix particles are sieved and mixed with 0.86% w/w magnesium stearate.

C) Compression of Tablets

Tablet (1)—1286 mg granules are pressed to tablet (equivalent to 1000 mg niacin) using 20.3×9.8 mm oval punches.

Tablet (2)—643 mg granules are pressed to tablet (equivalent to 500 mg niacin) using 14.95×8.35 mm oblong punches.

The dissolution rate of the novel dosage form was determined (Table 2)

TABLE 2

Dissolution profile

% Released

|    | Tablet (1) | Tablet (2) |
|----|------------|------------|
| 1  | 9.1        | 12.0       |
| 2  | 14.6       | 18.2       |
| 4  | 23.8       | 28.6       |
| 6  | 27.5       | 35.2       |
| 8  | 30.6       | 39.5       |
| 10 | 34.7       | 44.8       |
| 12 | 37.6       | 49.5       |
| 14 | 43.8       | 52.5       |
| 24 | 50.3       | 64.5       |

Dosage forms described in the examples 3 and 4 are prepared by not coating the micro matrix particles but the hydrophobic release controlling agent is mixed with the micro matrix particles. The sole purpose of these examples is to demonstrate the usefulness of the present invention as described earlier. The examples clearly show that the rate of release of the modified release active ingredient is significantly faster than the present invention.

Example 3

77.76% w/w of sodium valproate is mixed 7.78% w/w of Eudragit RS (Ammonio Methacrylate Copolymer type B USP) and the mixture is granulated with a solvent mixture of acetone and methylene chloride and then dried. The granules are sized and mixed with 13.6% w/w of hydrogenated castor oil and 0.86% w/w of magnesium stearate.

Compression of Tablets

Tablet (1)—1286 mg granules are pressed to tablet (equivalent to 1000 mg sodium valproate) using 20.3×9.8 mm oval punches.

Tablet (2)—643 mg granules are pressed to tablet (equivalent to 500 mg sodium valproate) using 14.95×8.35 mm oblong punches.

The dissolution rate of the novel dosage form was determined (Table 3)

TABLE 3

Dissolution profile

% Released

|   | Tablet (1) | Tablet (2) |
|---|------------|------------|
| 1 | 63.4       | 50.2       |
| 2 | 85.1       | 69.1       |
| 4 | 101.6      | 92.0       |
| 6 | 103.1      | 102.5      |

Example 4

77.76% w/w of niacin is mixed with 7.78% w/w of Eudragit RS (Ammonio Methacrylate Copolymer type B USP) and the mixture is granulated with a solvent mixture of acetone and methylene chloride and then dried. The granules are sized and mixed with 13.6% w/w of hydrogenated castor oil and 0.86% w/w of magnesium stearate.

Compression of Tablets

Tablet (1)—The granules are pressed to 1286 mg (equivalent to 1000 mg niacin) are compressed using 20.3×9.8 mm oval punches.

Tablet (2)—The granules are pressed to 643 mg (equivalent to 500 mg niacin) are compressed using 14.95×8.35 mm oblong punches.

The dissolution rate of the novel dosage form was determined (Table 4)

TABLE 4

Dissolution profile

| | % Released | |
|---|---|---|
| | Tablet (1) | Tablet (2) |
| 1 | 31.9 | 29.6 |
| 2 | 44.8 | 34.9 |
| 4 | 60.3 | 51.7 |
| 6 | 71.7 | 62.1 |
| 8 | 81.4 | 67.7 |
| 10 | 88.2 | 74.7 |
| 12 | 94.7 | 82.3 |
| 24 | 98.6 | 98.1 |

Example 5

A) Micro matrix particles—80.93% w/w of venlafaxine hydrochloride is mixed with 19.07% w/w of Eudragit RS (Ammonio Methacrylate Copolymer type B USP) and the mixture is granulated with a solvent mixture of acetone and methylene chloride and then dried. The granules are sized.

B) Coating of Micro matrix particles—70.13% w/w of micro matrix particles is charged in fluidized bed processor. 28.37% w/w of hydrogenated castor oil is dissolved in acetone and this coating solution is sprayed to coat the micro matrix particles. The coated micro matrix particles are sieved and mixed with 1.0% w/w magnesium stearate and 0.50% w/w colloidal silicon dioxide.

C) Compression of tablets—299.09 mg granules are pressed to tablet (equivalent to 150 mg venlafaxine) 9.53 mm round, concave punches.

The dissolution rate of the novel dosage form was determined (Table 5)

TABLE 5

Dissolution profile

| Time (hour) | % Released |
|---|---|
| 2 | 32.1 |
| 4 | 41.8 |
| 6 | 50.3 |
| 8 | 62.5 |
| 12 | 68.4 |

Example 6

A) Micro matrix particles—95.24% w/w of niacin is mixed with 4.76% w/w of Eudragit RS (Ammonio Methacrylate Copolymer type B USP) and the mixture is granulated with a solvent mixture of acetone and methylene chloride and then dried. The granules are sized.

B) Coating of Micro matrix particles—92.43% w/w of micro matrix particles is charged in fluidized bed processor. 6.60% w/w of hydrogenated castor oil is dissolved in acetone and this coating solution is sprayed to coat the micro matrix particles. The coated micro matrix particles are sieved and mixed with 0.97% w/w magnesium stearate.

C) Compression of tablets—1136 mg granules are pressed to tablet (equivalent to 1000 mg niacin) using 20.3×9.8 mm oval punches.

The dissolution rate of the novel dosage form was determined (Table 6)

TABLE 6

Dissolution profile

| Time (hour) | % Released |
|---|---|
| 1 | 24.87 |
| 2 | 35.25 |
| 4 | 48.71 |
| 6 | 57.80 |
| 8 | 64.61 |
| 10 | 72.22 |
| 12 | 77.20 |

Example 7

A) Micro matrix particles—Same as example 6.

B) Coating of Micro matrix particles—90.44% w/w of micro matrix particles is charged in fluidized bed processor. 8.61% w/w of hydrogenated castor oil is dissolved in acetone and this coating solution is sprayed to coat the micro matrix particles. The coated micro matrix particles are sieved and mixed with 0.95% w/w magnesium stearate.

C) Compression of tablets—1161 mg granules are pressed to tablet (equivalent to 1000 mg niacin) using 20.3×9.8 mm oval punches.

The dissolution rate of the novel dosage form was determined (Table 7)

TABLE 7

Dissolution profile

| Time (hour) | % Released |
|---|---|
| 1 | 24.35 |
| 2 | 36.41 |
| 4 | 43.86 |
| 6 | 50.63 |
| 8 | 57.43 |
| 10 | 63.82 |
| 12 | 71.20 |

Example 8

A) Micro matrix particles—90.91% w/w of metformin hydrochloride is mixed with 9.09% w/w of Eudragit RS (Ammonio Methacrylate Copolymer type B USP) and the mixture is granulated with a solvent mixture of acetone and methylene chloride and then dried. The granules are sized.

B) Coating of Micro matrix particles—85.54% w/w of micro matrix particles is charged in fluidized bed processor. 13.61% w/w of hydrogenated castor oil is dissolved in acetone and this coating solution is sprayed to coat the micro matrix particles. The coated micro matrix particles are sieved and mixed with 0.86% w/w magnesium stearate.

C) Compression of Tablets

Tablet (1)—1286 mg granules are pressed to tablet (equivalent to 1000 mg metformin hydrochloride) are compressed using 20.3×9.8 mm oval punches.

Tablet (2)—643 mg granules are pressed to tablet (equivalent to 500 mg metformin hydrochloride) are compressed using 14.95×8.35 mm oblong punches.

The dissolution rate of the novel dosage form was determined (Table 8)

TABLE 8

| | Dissolution profile | |
|---|---|---|
| | % Released | |
| | Tablet (1) | Tablet (2) |
| 1 | 37.1 | 36.5 |
| 2 | 49.5 | 51.0 |
| 4 | 65.3 | 63.6 |
| 6 | 76.2 | 77.5 |
| 8 | 84.0 | 87.8 |
| 10 | 91.7 | 91.9 |
| 12 | 98.9 | 95.8 |

Example 9

A) Micro matrix particles—90.91% w/w of metformin hydrochloride is mixed with 9.09% w/w of Eudragit RS (Ammonio Methacrylate Copolymer type B USP) and the mixture is granulated with a solvent mixture of acetone and methylene chloride and then dried. The granules are sized.

B) Coating of Micro matrix particles—83.91% w/w of micro matrix particles is charged in fluidized bed processor. 15.26% w/w of hydrogenated castor oil is dissolved in acetone and this coating solution is sprayed to coat the micro matrix particles. The coated micro matrix particles are sieved and mixed with 0.84% w/w magnesium stearate.

C) Compression of Tablets 1311 mg granules are pressed to tablet (equivalent to 1000 mg metformin hydrochloride) using 20.3×9.8 mm oval punches.

The dissolution rate of the novel dosage form was determined (Table 9)

TABLE 9

| Dissolution profile | |
|---|---|
| Time (hour) | % Released |
| 1 | 33.44 |
| 2 | 45.79 |
| 4 | 55.28 |
| 6 | 60.45 |
| 8 | 66.10 |
| 10 | 69.87 |
| 12 | 73.88 |
| 24 | 86.97 |

A) Micro matrix particles—90.91% w/w of metformin hydrochloride is mixed with 9.09% w/w of Eudragit RS (Ammonio Methacrylate Copolymer type B USP) and the mixture is granulated with a solvent mixture of acetone and methylene chloride and then dried. The granules are sized.

B) Coating of Micro matrix particles—87.23% w/w of micro matrix particles is charged in fluidized bed processor. 11.90% w/w of hydrogenated castor oil is dissolved in acetone and this coating solution is sprayed to coat the micro matrix particles. The coated micro matrix particles are sieved and mixed with 0.87% w/w magnesium stearate.

C) Compression of Tablets 1261 mg granules are pressed to tablet (equivalent to 1000 mg metformin hydrochloride) using 20.3×9.8 mm oval punches.

The dissolution rate of the novel dosage form was determined (Table 10)

TABLE 10

| Dissolution profile | |
|---|---|
| Time (hour) | % Released |
| 1 | 42.1 |
| 2 | 51.30 |
| 4 | 66.60 |
| 6 | 78.80 |
| 8 | 84.60 |
| 10 | 91.00 |
| 12 | 99.70 |

Dosage forms described in the example 11 are prepared by not coating the micro matrix particles but the hydrophobic release controlling agent is mixed with the micro matrix particles. The sole purpose of these examples is to demonstrate the usefulness of the present invention as described earlier. The examples clearly show that the rate of release of the modified release antidiabetic active ingredient is significantly faster than the present invention.

Example 11

77.76% w/w of metformin hydrochloride is mixed with 7.78% w/w of Eudragit RS (Ammonio Methacrylate Copolymer type B USP) and the mixture is granulated with a solvent mixture of acetone and methylene chloride and then dried. The granules are sized and mixed with 13.6% w/w of hydrogenated castor oil and 0.86% w/w of magnesium stearate.

Compression of Tablets

Tablet (1)—1286 mg granules are pressed to tablet (equivalent to 1000 mg metformin hydrochloride) using 20.3×9.8 mm oval punches.

Tablet (2)—643 mg granules are pressed to tablet (equivalent to 500 mg metformin hydrochloride) using 14.95×8.35 mm oblong punches.

The dissolution rate of the novel dosage form was determined (Table 11)

TABLE 11

| | Dissolution profile | |
|---|---|---|
| | % Released | |
| | Tablet (1) | Tablet (2) |
| 1 | 50.3 | 52.5 |
| 2 | 70.5 | 74.2 |
| 4 | 88.0 | 89.4 |
| 6 | 100.9 | 100.7 |

Example 12

A) Micro matrix particles—93.02% w/w of metformin hydrochloride is mixed with 6.98% w/w of Eudragit RS (Ammonio Methacrylate Copolymer type B USP) and the mixture is granulated with a solvent mixture of acetone and methylene chloride and then dried. The granules are sized.

B) Coating of Micro matrix particles—90.56% w/w of micro matrix particles is charged in fluidized bed processor. 8.42% w/w of hydrogenated castor oil is dissolved in acetone and this coating solution is sprayed to coat the micro matrix particles. The coated micro matrix particles are sieved and mixed with 1.01% w/w magnesium stearate.

C) Compression of Tablets 1187 mg granules are pressed to tablet (equivalent to 1000 mg metformin hydrochloride) using 20.3×9.8 mm oval punches.

The dissolution rate of the novel dosage form was determined (Table 12)

TABLE 12

| Dissolution profile | |
|---|---|
| Time (hour) | % Released |
| 1 | 37.59 |
| 2 | 48.91 |
| 4 | 59.24 |
| 6 | 74.85 |
| 8 | 86.15 |
| 10 | 88.48 |
| 12 | 93.30 |

Example 13

A) Micro matrix particles—Same as of example 12.

B) Coating of Micro matrix particles—88.70% w/w of micro matrix particles is charged in fluidized bed processor. 10.31% w/w of hydrogenated castor oil is dissolved in acetone and this coating solution is sprayed to coat the micro matrix particles. The coated micro matrix particles are sieved and mixed with 0.99% w/w magnesium stearate.

C) Compression of Tablets 1212 mg granules are pressed to tablet (equivalent to 1000 mg metformin hydrochloride) using 20.3×9.8 mm oval punches.

The dissolution rate of the novel dosage form was determined (Table 13)

TABLE 13

| Dissolution profile | |
|---|---|
| Time (hour) | % Released |
| 1 | 31.84 |
| 2 | 44.66 |
| 4 | 50.55 |
| 6 | 65.29 |
| 8 | 73.29 |
| 10 | 79.80 |
| 12 | 85.90 |

Example 14

A) Micro matrix particles—Same as of example 12.

B) Coating of Micro matrix particles—92.51% w/w of micro matrix particles is charged in fluidized bed processor. 6.45% w/w of hydrogenated castor oil is dissolved in acetone and this coating solution is sprayed to coat the micro matrix particles. The coated micro matrix particles are sieved and mixed with 1.03% w/w magnesium stearate.

C) Compression of Tablets 1162 mg granules are pressed to tablet (equivalent to 1000 mg metformin hydrochloride) using 20.3×9.8 mm oval punches.

The dissolution rate of the novel dosage form was determined (Table 14)

TABLE 14

| Dissolution profile | |
|---|---|
| Time (hour) | % Released |
| 1 | 45.90 |
| 2 | 60.10 |
| 4 | 77.00 |
| 6 | 89.70 |
| 8 | 96.72 |
| 10 | 98.57 |
| 12 | 104.33 |

Example 15

A) Micro matrix particles—Same as of example 12.

B) Coating of Micro matrix particles—91.33% w/w of micro matrix particles is charged in fluidized bed processor. 7.65% w/w of hydrogenated castor oil is dissolved in acetone and this coating solution is sprayed to coat the micro matrix particles. The coated micro matrix particles are sieved and mixed with 1.02% w/w magnesium stearate.

C) Compression of Tablets 1177 mg granules are pressed to tablet (equivalent to 1000 mg metformin hydrochloride) using 20.3×9.8 mm oval punches.

The dissolution rate of the novel dosage form was determined (Table 15)

TABLE 15

| Dissolution profile | |
|---|---|
| Time (hour) | % Released |
| 1 | 44.00 |
| 2 | 58.80 |
| 4 | 71.30 |
| 6 | 84.10 |
| 8 | 91.93 |
| 10 | 95.34 |
| 12 | 98.59 |

Example 16

Establishing the Pharmacokinetic Profile of Metformin Sustained Release Formulation The study was carried out to evaluate the pharmacokinetic parameters of the sustained release metformin formulation prepared as per the examples described above.

Methodology:

The biostudy had an open label, single period, single treatment, single dose study design.

Non-compartmental Pharmacokinetic assessment was based on the plasma levels of metformin. Blood samples were obtained before dosing and at the following times after administration of test formulation;

Pre-dose, 0.5, 0.75, 1.0, 1.5, 2.0, 3.0, 3.5, 4.0, 5.0, 6.0, 8.0, 10.0, 12.0, 15.0, 18.0, and 24.0 hours.

Study Population:

Healthy male volunteers aged between 18 to 45 years.

Number of Subjects:

Four (04) volunteers were enrolled and all of them completed the study. All 04 volunteers were included in the Pharmacokinetic and safety analyses.

Test Formulation, Dose and Mode of Administration:

Test Formulation: 1000 mg Metformin sustained release (SR) formulation prepared as per the invention disclosed. Volunteers received a single oral dose of the above product with 200 ml of water 30 minutes after a following high calorie breakfast (~800 Kcal).

Pharmacokinetics:

The following Pharmacokinetic parameters were calculated using non compartments methods: the area under the drug plasma concentration curve from time of dosing to the time of last sampling point ($AUC_{(0-t)}$); the area under the drug plasma concentration versus time curve extrapolated to infinity ($AUC_{(0-Inf.)}$); the maximum measured concentration of the drug in the plasma ($C_{max}$) and the time at which this concentration was measured ($t_{max}$); the concentration at 24 hours ($C_{24\,h}$); the time taken for drug plasma concentration to decrease by 50% ($t_{1/2}$); and the terminal first-order elimination rate constant ($K_{el}$).

Area Under the curve (AUC) is the integral part of drug blood level over time from zero to infinity and is a measure of quantity of drug absorbed and in the body.

AUC(0-t) represents area under the curve from zero to time t, where t represents the time at which last blood sample was taken.

$AUC_{(0-Inf)}$ represents area under the curve from zero to infinity.

Elimination half life of a drug is the time in hours necessary to reduce the drug concentration in the blood, plasma or serum to ½ after equilibrium is reached.

$C_{max}$ is the peak plasma concentration achieved after the administration of the drug.

$T_{max}$ is the time to reach peak plasma concentration.

Statistical Methods:

Descriptive statistics of relevant Pharmacokinetic parameters were performed.

Methods Used for Analysis of Metformin in Plasma Samples:

Estimation of Metformin in plasma samples was carried out by High Performance Liquid Chromatography and UV detection at 234 nm. Briefly 0.5 ml of plasma sample was precipitated with 2.0 ml acetonitrile. Samples were centrifuged and supernatant aliquot was washed with dichloromethane. After centrifugation, aqueous layer was injected on HPLC.

Figure 5:
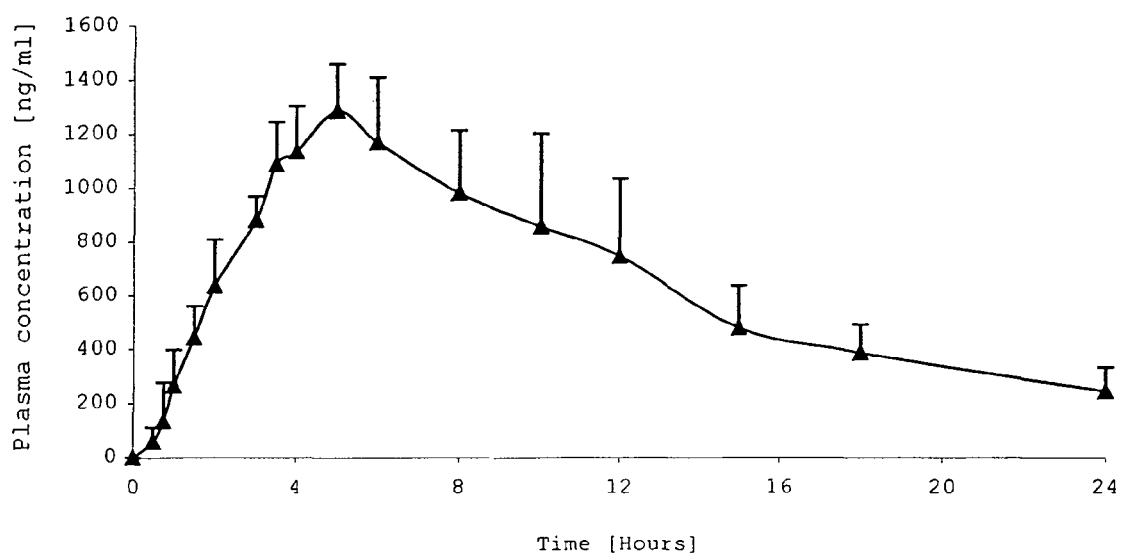
FIG. 5 is a plot of metformin plasma concentration versus time for formulation prepared as per the invention.

Pharmacokinetic Results:

The summary of the Pharmacokinetic parameters is contained in Table 16. The mean plasma concentration versus time curve is depicted in FIG. 5.

TABLE 16

Pharmacokinetic Parameters - Metformin SR (1000 mg)

| Parameters | Unit | Test (Mean ± SD) |
|---|---|---|
| $AUC_{0-inf}$ | ng * hr/ml | 18776 ± 4672 |
| $AUC_{0-24}$ | ng * hr/ml | 15424 ± 3428 |
| $C_{max}$ | ng/ml | 1348 ± 116 |
| $C_{24\,h}$ | ng/ml | 245 ± 90 |
| $T_{max}$ | hr | 4.88 ± 1.03 |
| $T_{1/2}$ | hr | 9.28 ± 1.73 |

Conclusion:

Metformin has shown sustained release characteristics with following Pharmacokinetic profile;

The $AUC_{0-24}$ ranged from 12395 to 20345 ng*hr/ml.

The $AUC_{0-Inf}$ ranged from 15791 to 25727 ng*hr/ml.

The $C_{max}$ ranged from 1227 to 1452 ng/ml.

The $C_{24h}$ ranged from 165 to 373 ng/ml.

The $T_{max}$ ranged from 3.50 to 6.00 hours.

The $T_{1/2}$ ranged from 7.13 to 11.19 hours.

Example 17

1) Production of Inner Portion 69.61% w/w of Aspirin coated granules (Aspirin 96% w/w, 2.0% w/w hydrogenated castor oil & 2.0% w/w citric acid anhydrous coated) mixed with the mixture of 11.56% w/w of microcrystalline cellulose (PH112, dried), 7.17% w/w sodium starch Glycolate (dried), 2.24% w/w citric acid anhydrous, 4.48% w/w talc, 1.79% w/w colloidal silicon dioxide, 1.79% w/w stearic acid and 1.35% w/w hydrogenated vegetable oil.

2) Production of Outer Portion

A) Micro matrix particles—93.02% w/w of nicotinic acid is mixed with 6.98% w/w of Eudragit RS PO (Ammonio Methacrylate Copolymer type B USP) and the mixture is granulated with a solvent mixture of acetone and methylene chloride and then dried. The granules are sized through 1.0 mm screen.

B) Coating of Micro matrix particles—92.67% w/w of micro matrix particles is charged in fluidized bed processor. 6.47% w/w of hydrogenated castor oil is dissolved in acetone and this coating solution is sprayed to coat the micro matrix particles. The coated micro matrix particles are sieved and mixed with 0.86% w/w magnesium stearate.

3) Compression of Bilayered Tablets 483.17 mg granules of inner portion (equal to 325.0 mg aspirin) and 1160 mg granules of outer portion (equal to 1000 mg nicotinic acid) are compressed into bilayered tablets using 20.3×9.8 mm oblong shaped punches.

What is claimed is:

1. A process for the preparation of a modified release dosage form comprising metformin hydrochloride prepared by using dual retard technique to control the release of metformin, wherein the said dual retard technique is a combination of a matrix formulation and a reservoir formulation, said process comprising:

a) preparing micro matrix particles consisting of metformin hydrochloride and one or more hydrophobic release controlling agents consisting of poly(ethyl acrylate, methyl methacrylate, trimethylammonioethyl methacrylate chloride) 1:2:O.1; poly(ethyl acrylate, methyl methacrylate, trimethylamonioethyl methacrylate chloride) 1:2:0.2; and poly(ethyl acrylate, methyl methacrylate) 2:1; and b) coating said micro matrix articles with one or more hydrophobic release controlling agents selected from the group consisting of waxes selected from the group consisting of beeswax, carnauba wax, microcrystalline wax, and ozokerite; fatty alcohols selected from the group consisting of cetostearyl alcohol, stearyl alcohol; cetyl alcohol and myristyl alcohol; and fatty acid esters selected from the group consisting of glyceryl monostearate; glycerol monooleate, acetylated monoglycerides, tristearin, tripalmitin, cetyl esters wax, glyceryl palmitostearate, glyceryl behenate and hydrogenated castor oil.

2. A process according to claim 1, wherein said micro matrix particles contain metformin hydrochloride and one or more hydrophobic release controlling agents are present in a weight ratio of from 100:2.5 to 100:30.

3. A process according to claim 1 wherein in said micro matrix particles, metformin hydrochloride can be less than or equal to 1500 mg.

4. A process according to claim 1, wherein said micro matrix particles and coating of one or more of said hydrophobic release controlling agents are present in a weight ratio of from 100:1 to 100:30.

* * * * *